US008957022B2

(12) United States Patent
Van Slyke et al.

(10) Patent No.: US 8,957,022 B2
(45) Date of Patent: *Feb. 17, 2015

(54) MULTIMERIC TIE 2 AGONISTS AND USES THEREOF IN STIMULATING ANGIOGENESIS

(75) Inventors: Paul Van Slyke, Toronto (CA); Daniel Dumont, Oakville (CA)

(73) Assignee: Sunnybrook Health Sciences Centre, Toronto (CA)

(*) Notice: Subject to any disclaimer, the term of this patent is extended or adjusted under 35 U.S.C. 154(b) by 1033 days.

This patent is subject to a terminal disclaimer.

(21) Appl. No.: 12/446,511

(22) PCT Filed: Oct. 26, 2007

(86) PCT No.: PCT/CA2007/001903
§ 371 (c)(1),
(2), (4) Date: Jan. 5, 2011

(87) PCT Pub. No.: WO2008/049227
PCT Pub. Date: May 2, 2008

(65) Prior Publication Data
US 2011/0097300 A1 Apr. 28, 2011

Related U.S. Application Data

(60) Provisional application No. 60/854,950, filed on Oct. 27, 2006.

(51) Int. Cl.
*A61K 47/48* (2006.01)
*A61K 38/17* (2006.01)
*A61K 38/04* (2006.01)
*A61L 27/60* (2006.01)
*C12Q 1/48* (2006.01)
*G01N 33/94* (2006.01)
*A61K 38/18* (2006.01)

(52) U.S. Cl.
CPC ....... *A61K 47/48215* (2013.01); *A61K 38/1709* (2013.01); *A61K 47/48238* (2013.01); *A61L 27/60* (2013.01); *C12Q 1/485* (2013.01); *G01N 33/94* (2013.01); *A61K 38/1866* (2013.01)
USPC ............ 514/7.5; 530/323; 530/326; 530/327; 530/328; 530/329

(58) Field of Classification Search
None
See application file for complete search history.

(56) References Cited

U.S. PATENT DOCUMENTS 6,365,154 B1 * 4/2002 Holmes et al. ............. 424/133.1
6,455,035 B1 9/2002 Suri et al.
2005/0100906 A1 5/2005 Davis et al.

FOREIGN PATENT DOCUMENTS

WO 0037642 6/2000
WO 0147951 7/2001
WO 03106501 12/2003
WO 2006005361 1/2006

OTHER PUBLICATIONS

Cho et al. "COMP-Ang1: A designed angiopoietin-1 variant with nonleaky angiogenic activity" PNAS, 2004, 101(15), 5547-5552.
Cho et al. "COMP-angiopoietin-1 promotes wound healing through enhanced angiogenesis, lymphangiogenesis and blood flow in a diabetic mouse model" PNAS, Mar. 28, 2006, 103(13), 4946-4951.
Kim et al. "Oligomerization and multimerization are critical for angiopoietin-1 to bind and phosphorylate Tie2", The Journal of Biological Chemistry, 2005, 280(20), 20126-20131.
Kim et al. "COMP-angiopoietin ameliorates renal fibrosis in a unilateral ureteral obstruction model" Journal of the American Society of Nephrology, 2006, 17, 2474-2483.
Kwak et al. "Angiopoietin-1 inhibits irradiation- and mannitol-induced apoptosis in endothelial cells" Circulation, 2000, 101, 2317-2324.
Peirce et al. "Spatial and temporal control of angiogenesis and arterialization using applications of VEGF164 and Ang-1*" Am. J. Physiol. Heart Circ. Physiol., 2004, 286, H918-H925.
Procopio et al. "Angiopoietin-1 and -2 coiled domains mediate distinct homo-oligomerization patterns but fibrinogen-like domains mediate ligand activity" The Journal of Biological Chemistry, 1999, 274(42), 30196-30201.
Wu et al. "A novel small peptide as a targeting ligand for receptor tyrosine kinase Tie2" Biochemical and Biophysical Research Communications, 2004, 315, 1004-1010.
Roselyne Tournaire et al., A short synthetic peptide inhibits signal transduction, migration and angiogenesis mediated by Tie2 receptor, EMBO reports, vol. 5, No. 3, 2004.
Nicole L. Ward et al., Functional inhibition of secreted angiopoietin: a novel role for angiopoietin 1 in coronary vessel patterning, Biochemical and Biophysical Research Communications 323 (2004) 937-946.
Samuel Davis et al., Angiopoietins have distinct modular domains essential for receptor binding, dimerization and superclustering, Nature Structural Biology, vol. 10, No. 1, Jan. 2003.

* cited by examiner

Primary Examiner — Marianne P Allen
(74) Attorney, Agent, or Firm — Bereskin & Parr LLP; Melanie Szweras

(57) ABSTRACT

The present invention provides a multimeric form of a Tie 2 binding peptide monomer, wherein the multimeric form has Tie 2 agonist activity. The multimeric form, preferably a tetramer, stimulates angiogenesis and promotes wound healing. The present invention also features pharmaceutical compositions comprising the multimeric Tie 2 agonists, including those suitable for topical or systemic administration. Methods of using the multimeric Tie 2 agonists of the invention for stimulating angiogenesis and for promoting healing of wounds, such as diabetic ulcers or skin grafts, are also provided.

13 Claims, 23 Drawing Sheets

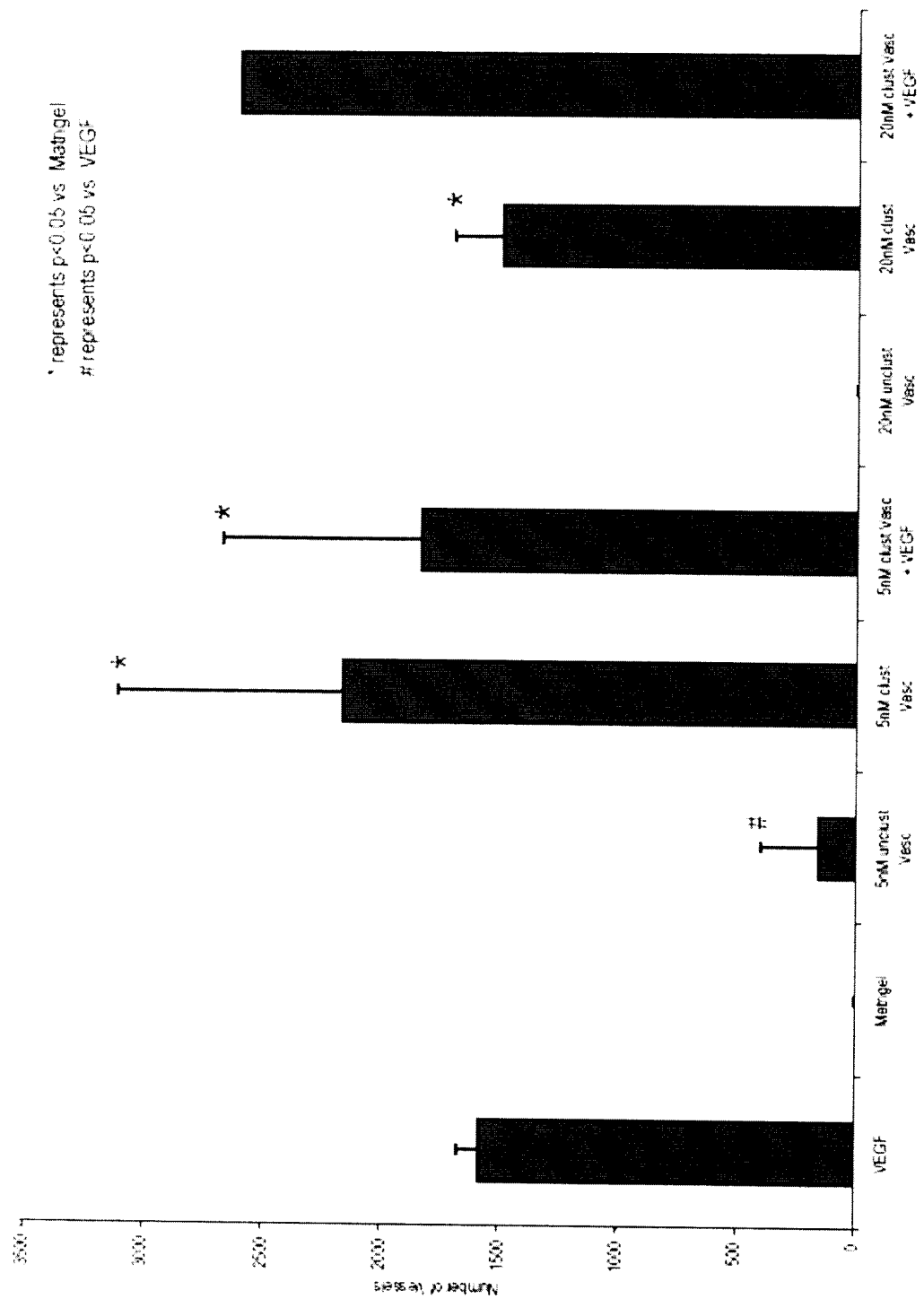

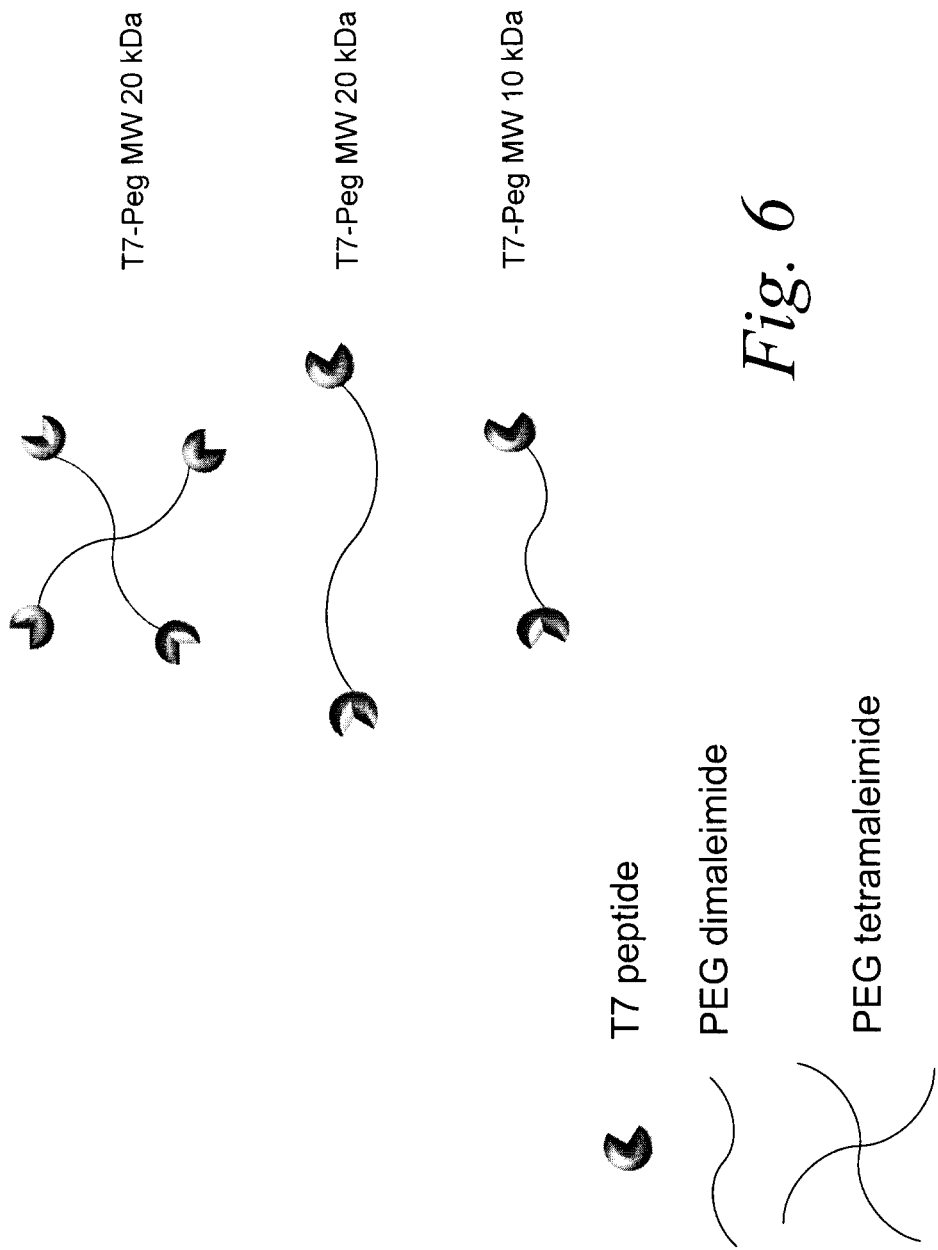

SEQUENCE LISTING

```
<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His His His Arg His Ser Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys His His His Arg His Ser Phe
1               5

<210> SEQ ID NO 3
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Thr Ile Ile Gln Arg Arg Glu Asp Gly Ser Val Asp Phe Gln Arg
 1               5                  10                  15

Thr Trp Lys Glu Tyr Lys
            20

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Trp Thr Ile Ile Gln Arg Arg Glu Asp Gly Ser Val Asp Phe Gln
 1               5                  10                  15

Arg Thr Trp Lys Glu Tyr Lys
            20

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Pro Trp Leu Thr Arg His
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys His Pro Trp Leu Thr Arg His
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Leu Trp Val Ile Pro Lys
 1               5

<210> SEQ ID NO 8
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 8

Cys Lys Leu Trp Val Ile Pro Lys
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Leu Leu Met Ala Ala Ser
  1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Asn Leu Leu Met Ala Ala Ser
  1               5
```

MULTIMERIC TIE 2 AGONISTS AND USES THEREOF IN STIMULATING ANGIOGENESIS

BACKGROUND OF THE INVENTION

Angiogenesis is the process by which new blood vessels are generated. Many of the signaling pathways that drive the angiogenic response originate at the plasma membrane and emanate from the activation of endothelial cell receptor tyrosine kinases, including Tie2/Tek (Jones, N. et al. (2001) *Nat. Rev. Mol. Cell. Biol.* 4:257-267; Olsson, A. et al. (2006) *Nat. Rev. Mol. Cell. Biol.* 5:359-371). Angiopoietin (Ang) members 1-4 constitute a family of protein growth factors, all of which have been shown to activate Tie 2 receptor activity to differing extents.

All the Ang's are characterized structurally by an N-terminal super clustering domain (SCD) followed by a coiled-coil domain (CCD) and a C-terminal fibrinogen-like domain (FLD) (Ward, N. and Dumont, D. (2002) *Semin. Cell. Dev. Biol.* 1:19-27) and (Tsigkos, K. et al. (2003) *Expert Opin. Investig. Drugs* 6:933-941). Functional studies have highlighted a role for the SCD and CCD's in forming high order homotypic Ang multimers (Procopio, W. et al. (1999) *J. Biol. Chem.* 42:30196-30201). The specific nature of these multimers is variable and seems to be unique to each Ang family member. Binding specificity of the Ang's for the Tie 2 receptor has been ascribed to the FLD. Taken together, unique structural attributes of each Ang family member promotes binding and differential clustering of Tie 2. The pleiotropic physiological effects of Ang 1-4 are thought to at least in part be mediated by appropriate and specific clustering of the receptor (Davis, S. et. al. (2003) *Nat. Struct. Biol.* 1:38-44; Procopio, W. et. al. (1999) *J. Biol. Chem.* 42:30196-30201; Cho, C. et. al. (2004) *Proc. Natl. Acad. Sci. USA* 15:5547-5552; Ward, D. et. al. (2004) *Biochem. Biophys. Res. Commun.* 3:937-946; Kim, K-T. et al. (2005) *J. Biol. Chem.* 280: 20126-20131). Gene ablation and transgenic approaches in mice have highlighted an indispensable role for Ang 1 and 2 in the development and maintenance of the blood and lymphatic vascular systems as well as well as the hematopoietic system. Non-genetic studies of the Ang's have been hampered by the inherent difficulty associated with their purification, stability and solubility.

Chronic wounds represent a significant medical problem. For example, global estimates report that 12.5 million patients worldwide suffer from chronic wounds and a significant number of these individuals suffer from decubitus ulcers and diabetic foot ulcers. Wound healing involves a well choreographed series of molecular activities that ultimately lead to wound closure. These events are driven by three interrelated processes: inflammation, cellular proliferation and angiogenesis. Impaired angiogenesis is one of several primary defects reported in diabetic patients. These patients often suffer from impaired wound healing, and as such suffer significant morbidity associated with vascular compromise (Dinh, T. and Veves, A. (2005) *Curr. Pharm. Des.* 18:145-153).

Primary defects in growth factor secretion and/or proteolytic cleavage of growth factors in diabetic wounds has been reported suggesting therapeutic application of these factors may be beneficial (Wieman, T. et al. (1998) *Diabetes Care* 5:822-827; Tsang, M. et. al. (2003) *Diabetes Care* 6:1856-1861). However, to date, effective means for stimulating angiogenesis, such as for use in the treatment of chronic wounds, are still lacking. Accordingly, a need exists for agents that are effective in stimulating angiogenesis.

SUMMARY OF THE INVENTION

This invention provides multimeric Tie 2 agonists that have angiogenic activity and that can be used to promote wound healing. A Tie 2 agonist of the invention is an angiopoietin mimetic that comprises a multimeric form of a Tie 2 binding peptide monomer. The Tie 2 agonists of the invention have been demonstrated to specifically bind to and activate Tie 2, as evidenced by phosphorylation of Tie 2, and to activate signaling pathways that previously have been demonstrated to be downstream of Tie 2, including the MAPK, AKT and eNOS pathways. The Tie 2 agonists of the invention also have been demonstrated to stimulate angiogenesis, resulting in well arborized vessels. Moreover, when used to stimulate angiogenesis in combination with VEGF, the Tie 2 agonists have been shown to mitigate the tortuosity seen when angiogenesis is stimulated by VEGF alone. Using an in vivo model of wound healing, the Tie 2 agonists of the invention have been demonstrated to improve wound closure time, primarily through increased granulation tissue and neovascularization of the wound.

Accordingly, one aspect of the invention pertains to a composition comprising a multimeric form of a Tie 2 binding peptide monomer, wherein the multimeric form has Tie 2 agonist activity. Preferably, the Tie 2 binding peptide contained in the monomer binds to Tie 2 with high affinity but does not substantially inhibit binding of an angiopoietin (e.g., Ang 1) to Tie 2. In one embodiment, the Tie 2 binding peptide monomer comprises an amino acid sequence that is present in a native Tie 2 ligand. In another embodiment, the Tie 2 binding peptide monomer comprises an amino acid sequence that is not present in a native Tie 2 ligand. Preferred Tie 2 binding peptides for use in the monomers of the invention include, but are not limited to, a T7 peptide (SEQ ID NOs: 1 or 2), a GA3 peptide (SEQ ID NOs: 3 or 4), a T6 peptide (SEQ ID NOs: 7 or 8) and a T8 peptide (SEQ ID NOs: 5 or 6). In an alternative embodiment, the Tie 2 binding peptide used in the monomer competes with an angiopoietin (e.g., Ang 1) for binding to Tie 2. A non-limiting example of such a peptide is a T 4 peptide (SEQ ID NOs: 9 or 10).

In a preferred embodiment, the multimeric form is a tetramer. Alternatively, the multimeric form can be, for example, a dimer or a multimeric form that comprises six, eight, ten or twelve units of the Tie 2 binding peptide monomer. In yet other embodiments, the multimeric form comprises an odd number of units of the Tie 2 binding peptide monomer, such as three, five, seven, nine or eleven units.

In a preferred embodiment, the Tie 2 binding peptide monomer comprises a structure: A-B-C, wherein A comprises a Tie 2 binding peptide, B comprises a spacer and C comprises a multimerizing group, wherein C has affinity for D, a multimer agent comprising multiple binding sites for C. For example, the multimer agent D can have four binding sites for the multimerizing group C such that a tetramer is formed when four Tie 2 binding peptide monomers, A-B-C, interact with the multimer agent D. In a preferred embodiment, C comprises a biotin group and D comprises an agent selected from the group consisting of avidin, streptavidin and neutravidin. In another preferred embodiment, the spacer B comprises polyethylene glycol (PEG).

In another embodiment, the Tie 2 binding peptide monomer comprises a structure: A-B, wherein A comprises a Tie 2 binding peptide and B comprises a spacer, wherein the multimeric form is created by covalent linkage of multiple Tie 2 binding peptide monomers via the spacer B. In a preferred embodiment, the spacer B comprises polyethylene glycol (PEG).

In another embodiment, the multimeric form comprises a peptide dimer, comprising: (a) a first peptide chain; (b) a second peptide chain; and (c) a linking moiety connecting said first and second peptide chains, wherein said peptide dimer binds to and activates the Tie 2 receptor. Preferably, the first peptide chain is a T7 peptide (SEQ ID NOs: 1 or 2). Preferably, the second peptide chain is a T7 peptide (SEQ ID NOs: 1 or 2). More preferably, both the first and second peptide chains are T7 peptides (SEQ ID NOs: 1 or 2). Preferably, the linking moiety comprises one or more water soluble polymers covalently bound to the first peptide chain and the second peptide chain. More preferably, the one or more water soluble polymers are linear polymers. In a preferred embodiment, the water soluble polymer is a polyethylene glycol (PEG) (e.g., a linear PEG molecule). Preferably, the PEG has a molecular weight of less than about 20,000 Daltons. More preferably, the PEG has a molecular weight of in the range of about 3,000 Daltons to about 10,000 Daltons. In various embodiments, the PEG has a molecular weight of about 3,000 Daltons, about 3,400 Daltons, about 5,000 Daltons or about 10,000 Daltons.

In another embodiment, the multimeric form comprises a peptide tetramer, comprising: (a) a first peptide chain; (b) a second peptide chain; (c) a third peptide chain; (d) a fourth peptide chain; and (e) a linking moiety connecting said first, second, third and fourth peptide chains, wherein said peptide tetramer binds to and activates the Tie 2 receptor. Preferably, the first, second, third and fourth peptide chains are T7 peptides (SEQ ID NOs: 1 or 2). Preferably, the linking moiety comprises one or more water soluble polymers covalently bound to the first, second, third and fourth peptide chains. More preferably, the one or more water soluble polymers are branched chain polymers. In a preferred embodiment, the water soluble polymer is a polyethylene glycol (PEG) (e.g., a branched chain PEG molecule). Preferably, the branched PEG has a molecular weight in the range of about 3,000 Daltons to about 20,000 Daltons. In various embodiments, the branched PEG has a molecular weight of about 3,000 Daltons, about 3,400 Daltons, about 5,000 Daltons, about 10,000 Daltons or about 20,000 Daltons.

The multimeric forms of the invention exhibit Tie 2 agonist activity. For example, in one embodiment, the multimeric form stimulates Tie 2 phosphorylation. In another embodiment, the multimeric form stimulates phosphorylation of MAPK, AKT and eNOS. Preferably, a multimeric form of the invention has at least one effect on endothelial cells selected from the group consisting of: stimulation of endothelial cell migration, stimulation of MMP2 release from endothelial cells and protection of endothelial cells from serum withdrawal-induced apoptosis and even more preferably has all three effects on endothelial cells. Preferably, the multimeric form stimulates an angiogenic response in vivo in a Matrigel assay. Preferably, the multimeric form stimulates wound healing in a subject when applied topically to a wound of the subject.

In a particularly preferred embodiment, the invention provides a composition comprising a tetramer form of a Tie 2 binding peptide monomer, wherein the Tie 2 binding peptide monomer comprises a structure: A-B-C, wherein:
 A comprises a Tie 2 binding peptide selected from a T7 peptide (SEQ ID NOs: 1 or 2) and a GA3 peptide (SEQ ID NOs: 3 or 4);
 B comprises a polyethylene glycol spacer; and
 C comprises a biotin group, wherein four copies of A-B-C are associated with a tetramer agent, D, to create the tetramer form, the tetramer agent, D, being selected from the group consisting of avidin, streptavidin and neutravidin.

Another aspect of the invention pertains to pharmaceutical compositions comprising the multimeric form of a Tie 2 binding peptide monomer and a pharmaceutically acceptable carrier. In one embodiment, the pharmaceutically acceptable carrier is suitable for topical administration. In another embodiment, the pharmaceutically acceptable carrier is suitable for systemic administration.

Another aspect of the invention pertains to methods for making the multimeric forms of the invention. For example, the invention provides a method of making a Tie 2 binding peptide monomer comprising a structure: A-B-C, wherein:
 A comprises a Tie 2 binding peptide;
 B comprises a polyethylene glycol spacer; and
 C comprises a biotin group,
the method comprising reacting a Tie 2 binding peptide comprising an amino terminal amino acid residue comprising a first reactive group with a reagent comprising the structure: second reactive group-B-C, wherein the first reactive group reacts with the second reactive group, to form A-B-C. Still further, the invention provides a method of making a tetramer form of the Tie 2 binding peptide monomer A-B-C, the method comprising combining the Tie 2 binding peptide monomer, A-B-C, with a tetramer agent, D, at a 4:1 ratio, the tetramer agent, D, being selected from the group consisting of avidin, streptavidin and neutravidin.

Yet another aspect of the invention pertains to a method of detecting a multimeric form of the invention, wherein the detection method comprises contacting a composition of the invention with a monoclonal antibody that specifically binds to a Tie 2 binding peptide contained within the composition. For example, a composition of the invention comprising a T7 peptide can be detected using a monoclonal antibody that specifically binds to the T7 peptide. Monoclonal antibody compositions that specifically bind to the T7 peptide also are encompassed by the invention.

Yet another aspect of the invention pertains to a method of activating a Tie 2 receptor comprising contacting the Tie 2 receptor with the multimeric form of a Tie 2 binding peptide monomer of the invention such that the Tie 2 receptor is activated. Activation of the Tie 2 receptor can be evidenced by, for example, phosphorylation of residue tyrosine 992 (Y992) of the Tie 2 receptor or phosphorylation of MAPK, AKT or eNOS.

Yet another aspect of the invention pertains to a method of stimulating angiogenesis at a site in a subject comprising contacting the site with the multimeric form of a Tie 2 binding peptide monomer of the invention such that angiogenesis is stimulated at the site in the subject. The multimeric form can be contacted with the site by, for example, topical administration of the multimeric form or systemic administration of the multimeric form. Preferably, angiogenesis stimulated by the multimeric form is characterized by at least one of the following properties:
 a) recruitment of perivascular support cells;
 b) non-leakiness of vessels; and
 c) well-defined arborization.

In one embodiment of the method of stimulating angiogenesis, the method further comprises contacting the site in the subject with a second angiogenic agent, such as VEGF, PDGF, G-CSF, recombinant human erythropoietin, bFGF and placental growth factor (PLGF). The method of stimulating angiogenesis can be used in clinical situations such as vascularization of regenerative tissues, ischemic limb disease, cerebral ischemia, conditions of vascular inflammation, arteriosclerosis, avascular necrosis, stimulation of hair growth and erectile dysfunction.

Another aspect of the invention pertains to a method of decreasing vascular permeability at a site of leaky vessels. The method comprises contacting the site of leaky vessels with a multimeric form of a Tie 2 binding peptide monomer of the invention such that vascular permeability is decreased. The method of decreasing vascular permeability can be used in clinical situations such as stroke, macular degeneration, macular edema, lymph edema, breakdown of the blood-retinal barrier, breakdown of the blood-brain barrier and normalization of tumor vasculature.

Another aspect of the invention pertains to a method of protecting endothelial cells. The method comprises contacting the endothelial cells with a multimeric form of a Tie 2 binding peptide monomer of the invention such that the endothelial cells are protected. The method of protecting endothelial cells can be used in clinical situations such as kidney fibrosis, stroke, macular degeneration and diabetic complications.

Still another aspect of the invention pertains to a method of stimulating healing of a wound in a subject, the method comprising contacting the wound with the multimeric form of a Tie 2 binding peptide monomer of the invention such that healing of the wound is stimulated in the subject. The multimeric form can be contacted with the wound by, for example, topical administration of the multimeric form or systemic administration of the multimeric form. In a preferred embodiment, the wound is a diabetic ulcer. In other embodiments, the wound is, for example, a decubitus ulcer, a pressure ulcer, a surgical incision, a traumatic tissue injury, a burn or a skin graft.

The invention also provides various biomaterials into which is incorporated a multimeric form of a Tie 2 binding peptide monomer of the invention. The biomaterial can be, for example, Matrigel, a skin substitute or a cross-linked glycosaminoglycan hydrogel. In one embodiment of the biomaterial, a second agent is also incorporated into the biomaterial. Such a second agent can be, for example, VEGF, PDGF, G-CSF, recombinant human erythropoietin, bFGF or placental growth factor (PLGF).

BRIEF DESCRIPTION OF THE DRAWINGS

FIG. 3A is a bar graph of the results of a Matrigel assay, quantifying the number of vessels in each treatment group, showing that clustered Vasculotide, alone or in combination with VEGF, increases vessel number.

FIG. 6 is a schematic illustration of PEG-linked, T7 peptide-containing Tie 2 agonists, referred to herein as PEG-Vasculotide.

DETAILED DESCRIPTION OF THE INVENTION

Figure 1A:
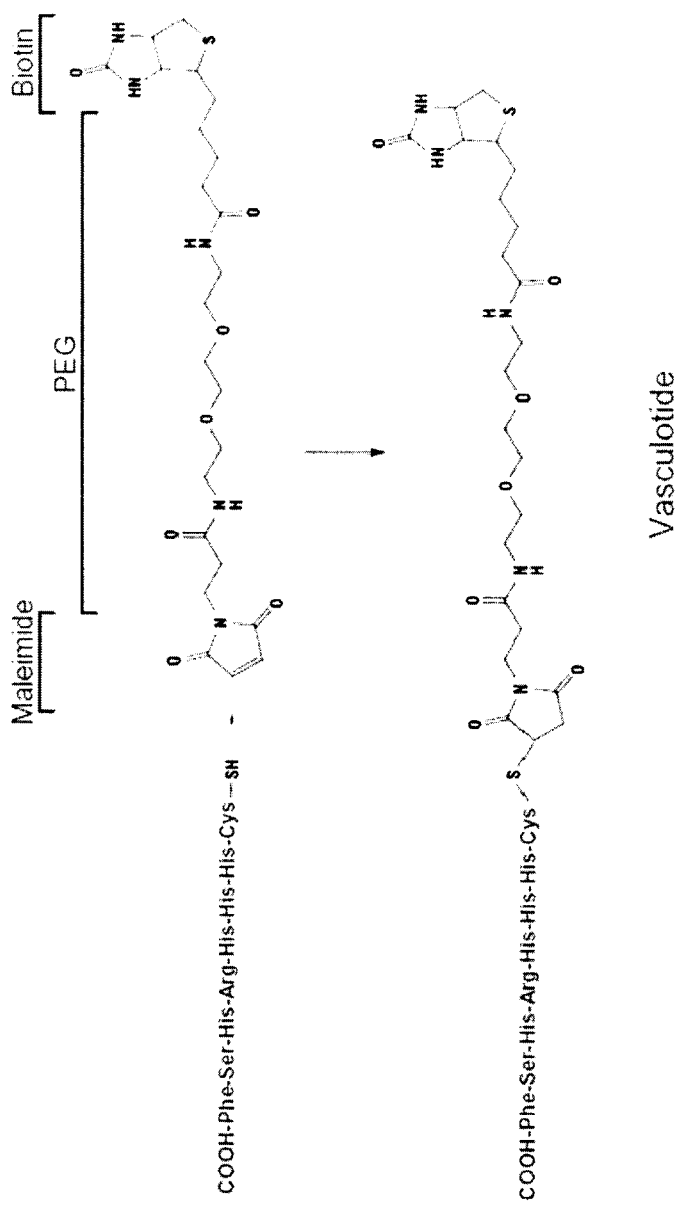
FIG. 1A is a schematic diagram of unclustered Vasculotide, prepared by linkage of the T7 peptide to a PEG-spacer containing biotin labelling reagent (Maleimide-PEO2-Biotin).

This invention pertains to multimeric forms of a Tie 2 binding peptide monomer and compositions and uses thereof. As demonstrated herein, when a peptide known to bind Tie 2 was multimerized, it was shown to be capable of activating Tie 2 and its associated signalling pathways. Moreover, this activation has been demonstrated to result in the production of angiogenic responses, both in vitro and in vivo. Still further, it has been demonstrated that activation of the pleiotropic Tie 2 signalling axis by the multimeric compound of the invention can produce blood vessels that are highly organized and well supported by myogenic support cells. Stimulation of wound healing by the multimeric form of the invention also has been demonstrated. Accordingly, the multimeric forms of the invention can be applied to a wide variety of situations in which stimulation of angiogenesis and/or wound healing is desireable.

Prior to further describing the invention, it may be helpful to an understanding thereof to set forth definitions of certain terms to be used herein As used herein, the term "Tie 2" refers to a receptor protein tyrosine kinase that is expressed almost exclusively on endothelial cells and that is also known in the art as TEK, p140 TEK, CD202B and VMCM. The term "Tie 2" is intended to encompass the receptor from any species that expresses this receptor, although human Tie 2 is preferred. The mRNA and protein sequences of human Tie 2 are set forth at GenBank Accession Nos. NM_000459 and NP_000450, respectively.

As used herein, the term "angiopoietin" is intended to refer to any one of a family of protein growth factors known to be ligands for Tie 2, including angiopoietin 1 (or Ang 1), angiopoietin 2 (or Ang 2), angiopoietin 3 (or Ang 3) and angiopoietin 4 (or Ang 4). The term "angiopoietin" is intended to encompass the growth factor from any species that expresses the growth factor, although human angiopoietin family members are preferred. The mRNA and protein sequences of human Ang 1 are set forth at GenBank Accession Nos. NM_001146 and NP_001137, respectively. The mRNA and protein sequences of human Ang 2 are set forth at GenBank Accession Nos. NM_001147 and NP_001138, respectively. The mRNA and protein sequences of human Ang 4 are set forth at GenBank Accession Nos. NM_015985 and NP_057069, respectively.

As used herein, the term "MAPK" is intended to refer to mitogen activated protein kinase, also known as ERK or extracellular signal-regulated kinase, an intracellular kinase that is phosphorylated upon activation of Tie 2. The term "MAPK" is intended to encompass the kinase from any species that expresses the kinase, although human MAPK is preferred. The mRNA and protein sequences of human MAPK are set forth at GenBank Accession Nos. NM_002736 and NP_002745, respectively.

As used herein, the term "AKT" is intended to refer to a protein kinase also known as v-akt murine thymoma viral oncogene homolog, an intracellular kinase that is phosphorylated upon activation of Tie 2. The term "AKT" is intended to encompass the kinase from any species that expresses the kinase, although human AKT is preferred. The mRNA and protein sequences of human AKT are set forth at GenBank Accession Nos. NM_001014431 and NP_001014431, respectively.

As used herein, the term "eNOS" is intended to refer to endothelial cell nitric oxide synthetase, also known as NOS 3, NOS III or ECNOS, an intracellular enzyme that is phosphorylated upon activation of Tie 2. The term "eNOS" is intended to encompass the enzyme from any species that expresses the enzyme, although human eNOS is preferred. The mRNA and protein sequences of human eNOS are set forth at GenBank Accession Nos. NM_000603 and NP_000594, respectively.

As used herein, the term "MMP2" is intended to refer to matrix metalloproteinase 2, a protein secreted by endothelial cells that is involved in the breakdown of extracellular matrix. The term "MMP2" is intended to encompass the protein from any species that expresses the protein, although human MMP2 is preferred. The mRNA and protein sequences of human MMP2 are set forth at GenBank Accession Nos. NM_004530 and NP_004521, respectively.

As used herein, the term "VEGF" is intended to refer to vascular endothelial growth factor, also known as VPF or vascular permeability factor, a growth factor involved in endothelial cell growth and angiogenesis. The term "VEGF" is intended to encompass the growth factor from any species that expresses the growth factor, although human VEGF is preferred. The mRNA and protein sequences of human VEGF (variant 1) are set forth at GenBank Accession Nos. NM_001025366 and NP_001020537, respectively.

As used herein, the term "PDGF" is intended to refer to platelet derived growth factor, a mitogenic factor for cells of mesenchymal origin. The term "PDGF" is intended to encompass the growth factor from any species that expresses the growth factor, although human PDGF is preferred. The protein has an alpha chain and a beta chain and can exist as a homodimer or a heterodimer. The mRNA and protein sequences of human PDGF alpha (isoform 1) are set forth at GenBank Accession Nos. NM_002607 and NP_002598, respectively. The mRNA and protein sequences of human PDGF beta (isoform 1) are set forth at GenBank Accession Nos. NM_002608 and NP_002599, respectively.

As used herein, the term "Tie 2 binding peptide" is intended to encompass peptides at least two amino acids in length and preferably no more than 100 amino acids in length that have binding affinity for Tie 2. The term "Tie 2 binding peptide" is not intended to encompass naturally occurring ligands for Tie 2, such as native, full-length angiopoietin proteins. Furthermore, the term "Tie 2 binding peptide" is intended to encompass peptides comprised in whole or in part of L-amino acids, peptides comprised in whole or in part of D-amino acids and peptides comprised of both L- and D-amino acids. Still further, the term "Tie 2 binding peptide" is intended to encompass peptides comprised in whole or in part of the 20 naturally-occurring amino acid residues, peptides comprised in whole or in part of non-naturally-occurring amino acid residues and peptide comprised of both naturally-occurring and non-naturally-occurring amino acid residues.

As used herein, the term "Tie 2 binding peptide monomer" is intended to refer to a single unit of a Tie 2 binding peptide compound. The Tie 2 binding peptide compound, or monomer, comprises the Tie 2 binding peptide, and may comprise other chemical moieties (e.g., spacers, multimerizing groups and the like), but the Tie 2 binding peptide monomer comprises only one copy (or unit) of the Tie 2 binding peptide and thus has a single valency for the Tie 2 receptor.

As used herein, the term "multimeric form" of a Tie 2 binding peptide monomer is intended to refer to forms that contain more than one unit of the Tie 2 binding peptide monomer such that the multimeric form (e.g., dimer, tetramer and the like) comprises more than one copy (or unit) of the Tie 2 binding peptide and thus has multivalency for the Tie 2 receptor.

As used herein, the term "high affinity", as used with respect to binding of a Tie 2 binding peptide to the Tie 2 receptor, is intended to mean binding of the peptide to the receptor with $K_d$ of about $10^{-3}$ M or less, more preferably $10^{-4}$ M or less, even more preferably $10^{-5}$ M or less.

As used herein, the term "does not substantially inhibit binding of an angiopoietin to Tie 2", as used with respect to a Tie 2 binding peptide, is intended to mean that the ability of the Tie 2 binding peptide to inhibit binding of an angiopoietin (e.g., Ang 1) to Tie 2 is essentially no greater than the ability of a unrelated, control peptide (e.g., a peptide that does not have measurable affinity for Tie 2) to inhibit the binding of an angiopoietin (e.g., Ang 1) to Tie 2.

As used herein, the term "Tie 2 agonist activity" is intended to refer to stimulating, enhancing, increasing or upregulating Tie 2 receptor activity, as measured by any method, technique, signal, detector or indicator that is known in the art to be indicative of Tie 2 receptor activity. Non-limiting examples of such indicators of Tie 2 activity include phosphorylation of human Tie 2 at amino acid residue Y992 or phosphorylation of one or more of MAPK, AKT and eNOS.

The invention is described in further detail in the following subsections, which subsections are presented only for purposes of clarity and should in no way be considered as limitations.

I. Multimeric Forms of Tie 2 Binding Peptide Monomers

This invention provides a composition comprising a multimeric form of a Tie 2 binding peptide monomer, wherein the multimeric form has Tie 2 agonist activity. Thus, the composition has two aspects to consider: the structure of the Tie 2 binding peptide monomer itself, and the means by which the monomer is multimerized to create the multimeric form that has Tie 2 agonist activity, both of which aspects will be discussed further herein. In one embodiment, the multimeric form comprises an even number of units of the monomer. In a preferred embodiment, the multimeric form is a tetramer. In another preferred embodiment, the multimeric form is a dimer. In yet other embodiments, the multimeric form comprises six, eight, ten or twelve units of the Tie 2 binding peptide monomer. In another embodiment, the multimeric form comprises an odd number of units of the monomer. For example, the multimer form can be a trimer or the multimeric form can comprises five, seven, nine or eleven units of the Tie 2 binding peptide monomer.

The Tie 2 binding peptide monomer comprises a peptide that has binding affinity for Tie 2. Furthermore, the monomer may comprise other chemical moieties, which are discussed in further detail below.

The Tie 2 binding peptide contained within the monomer is at least two amino acids in length, more preferably is at least five amino acids in length and even more preferably is at least seven amino acids in length. A preferred size range for the peptide is 7-25 amino acids in length, more preferably 7-15 amino acids in length. Other size ranges include 5-30 amino acids in length, 5-40 amino acids in length, 5-50 amino acids in length, 5-60 amino acids in length, 5-70 amino acids in length, 5-80 amino acids in length, 5-90 amino acids in length or 5-100 amino acids in length. Preferably, the peptide is no more than 100 amino acids in length.

In one embodiment, the Tie 2 binding peptide within the monomer comprises an amino acid sequence that is present in a native Tie 2 ligand (e.g., an angiopoietin, such as Ang 1 or Ang 2). For example, a fragment of an angiopoietin that retains the ability to bind to Tie 2 can be used as the Tie 2 binding peptide. Alternatively, in another embodiment, the Tie 2 binding peptide within the monomer comprises an amino acid sequence that is not present in a native Tie 2 ligand. It has been shown that peptides having amino acid sequences that differ from the primary sequence of angiopoietins can be selected that have affinity for Tie 2 (see e.g., Tournaire, R. et al. (2004) *EMBO Reports* 5:262-267). Such peptides can be identified, for example, by screening of a phage displayed peptide library (e.g., a random 7-mer library) for peptides that bind to Tie 2 (e.g., a Tie 2-Fc fusion protein), with confirmation of peptide binding to Tie 2 by screening of the selected peptide for binding to Tie 2 using an ELISA assay (e.g., as described in Tournaire, R. et al. (2004) supra).

It is preferable that the Tie 2 binding peptide used in the monomer binds to Tie 2 with high affinity but does not substantially inhibit binding of an angiopoietin to Tie 2. This embodiment is preferable so that the multimeric form does not compete with native angiopoietins for binding to Tie 2. For example, preferably the Tie 2 binding peptide binds to Tie 2 with high affinity but does not substantially inhibit the binding of Ang 1 to Tie 2. Additionally or alternatively, preferably the Tie 2 binding peptide binds to Tie 2 with high affinity but does not substantially inhibit the binding of, for example, Ang 2 or Ang 4, to Tie 2.

In a preferred embodiment, the Tie 2 binding peptide monomer comprises a T7 peptide, which T7 peptide comprises an amino acid sequence: His-His-His-Arg-His-Ser-Phe (SEQ ID NO: 1). In one embodiment, the T7 peptide has an amino terminal cysteine residue added to it and, thus, in this embodiment, the T7 peptide comprises an amino acid sequence: Cys-His-His-His-Arg-His-Ser-Phe (SEQ ID NO: 2).

In another preferred embodiment, the Tie 2 binding peptide monomer comprises a GA3 peptide, which GA3 peptide comprises an amino acid sequence: Trp-Thr-Ile-Ile-Gln-Arg-Arg-Glu-Asp-Gly-Ser-Val-Asp-Phe-Gln-Arg-Thr-Trp-Lys-Glu-Tyr-Lys (SEQ ID NO: 3). In one embodiment, the GA3 peptide has an amino terminal cysteine residue added to it and, thus, in this embodiment, the GA3 peptide comprises an amino acid sequence: Cys-Trp-Thr-Ile-Ile-Gln-Arg-Arg-Glu-Asp-Gly-Ser-Val-Asp-Phe-Gln-Arg-Thr-Trp-Lys-Glu-Tyr-Lys (SEQ ID NO: 4).

In yet another embodiment, the Tie 2 binding peptide monomer comprises a T8 peptide, which T8 peptide comprises an amino acid sequence: His-Pro-Trp-Leu-Thr-Arg-His (SEQ ID NO: 5). In one embodiment, the T8 peptide has an amino terminal cysteine residue added to it and, thus, in this embodiment, the T8 peptide comprises an amino acid sequence: Cys-His-Pro-Trp-Leu-Thr-Arg-His (SEQ ID NO: 6).

In yet another embodiment, the Tie 2 binding peptide monomer comprises a T6 peptide, which T6 peptide comprises an amino acid sequence: Lys-Leu-Trp-Val-Ile-Pro-Lys (SEQ ID NO: 7). In one embodiment, the T6 peptide has an amino terminal cysteine residue added to it and, thus, in this embodiment, the T6 peptide comprises an amino acid sequence: Cys-Lys-Leu-Trp-Val-Ile-Pro-Lys (SEQ ID NO: 8).

In an alternative embodiment, the Tie 2 binding peptide used in the monomer can comprises a peptide that competes with an angiopoietin (e.g., Ang 1) for binding to Tie 2. A non-limiting example of such a peptide is a T4 peptide, which T4 peptide comprises an amino acid sequence: Asn-Leu-Leu-Met-Ala-Ala-Ser (SEQ ID NO: 9). In one embodiment, the T4 peptide has an amino terminal cysteine residue added to it and, thus, in this embodiment, the T4 peptide comprises an amino acid sequence: Cys-Asn-Leu-Leu-Met-Ala-Ala-Ser (SEQ ID NO: 10).

The Tie 2 binding peptides T4, T6, T7 and T8 also are described in Tournaire, R. et al. (2004) *EMBO Reports* 5:262-267. The Tie 2 binding peptide GA3 also is described in Wu, X. et al. (2004) *Biochem. Biophys. Res. Commun.* 315:1004-1010.

In addition to the Tie 2 binding peptide, the Tie 2 binding peptide monomer can comprise other chemical moieties or groups, such as spacers and/or multimerizing groups. For example, the Tie 2 binding peptide can be linked to a spacer, which may serve one or more functionalities. The spacer can, for example, function to increase the distance between the monomers when they are multimerized to facilitate interaction of the multimeric form with the Tie 2 receptor (e.g., reduce steric hindrance). Additionally or alternatively, the spacer can, for example, serve as a chemical group by which the monomers can be multimerized. Moreover, the Tie 2 binding peptide monomer can comprise one or more multimerizing groups, chemical moieties that function to facilitate multimerization of the monomers. A preferred multimerizing group is a biotin group, which has affinity for avidin, streptavidin and neutravidin such that any of the three latter compounds can be used for multimerization of monomers comprising a biotin group. Another example of a multimerizing group is a coiled coil domain, which can be linked to the amino terminus of the peptide through standard recombinant DNA engineering techniques and which self-assembles into oligomeric structures (see e.g., U.S. Patent Publications 20030220476 and 20060074230 for further description of the use of coiled coil domains for multimerization). Non-limiting examples of coiled coil domains suitable for use are the coiled coil domains from the yeast transcription factor GCN4, from cartilage matrix protein (CMP) or from cartilage oligomeric matrix protein (COMP).

A preferred spacer is a polyethylene glycol (PEG) spacer, which is a polymeric molecule that can contain different numbers of units, such as 2, 4, 6, 8, 10, 11 or 12 units. PEG polymers are also known in the art as polyethylene oxide (PEO) polymers and thus the terms PEG and PEO as used herein are intended to be equivalent. Numerous other suitable spacers (also known as linkers) are well known in the art, non-limiting examples of which include other polyalkylene glycols, polyesters and polyalkylene amines. Moreover, a wide variety of spacers linked on one end to a reactive moiety and on the other end to a biotin group are commercially available (EZ-Link Biotin reagents available from Pierce Chemical Co., Rockford, Ill., USA) and can be used in the preparation of the Tie 2 binding peptide monomers of the invention. Non-limiting examples of commercially available reagents of the structure: reactive moiety-spacer-biotin include:

Sulfhydryl Reactive Reagents:
EZ-Link Biotin-BMCC (1-Biotinamido-4-(4'-[maleimidoethyl-cyclohexane]-carboxamido)butane)
EZ-Link Biotin-HPDP (N-(6-(Biotinamido)hexyl)-3'-(2'-pyridyldithio)-propionamide
EZ-Link Iodoacetyl-LC-Biotin (N-iodoacetyl-N-biotinyl-hexylenediamine)
EZ-Link Iodoacetyl-PEO$_2$ Biotin ((+)-Biotinyl-iodoacetamidyl-3,6-dioxaoctanediamine)
EZ-Link Maleimide PEO$_n$-Biotin (n=2 or 11)

Amine Reactive Reagents:
EZ-Link NHS-PEO$_n$-Biotin (n=4 or 12)
EZ-Link NHS-SS-Biotin (succinimidyl 2-(biotinamido)-ethyl-1,3'-dithiopropionate)
EZ-Link Sulfo-NHS-LC-Biotin (Sulfosuccinimidyl-6-(biotinamido)hexanoate)
EZ-Link TFP-PEO$_3$-Biotin (Tetrafluorophenyl Ester PEO$_3$-biotin)

Carboxyl Reactive Reagents:
EZ-Link 5-(Biotinamido)pentylamine
EZ-Link Amine-PEO$_2$-Biotin Labeling Reagent ((+)-Biotinyl-3,6-dioxaoctanediamine)
EZ-Link Amine-PEO$_3$-Biotin Labeling Reagent ((+)-Biotinyl-3,6,9-trioxaundecanediamine)
EZ-Link Biotin PEO-Amine ((+)-Biotinyl-3,6-dioxaoctanediamine)
EZ-Link Biotin-PEO-LC-Amine ((+)-Biotinyl-3,6,9-trioxaundecanediamine)

Furthermore, a branched arm spacer can be linked to multiple copies of the Tie 2 binding peptide as a means to multimerize the peptide. Non-limiting examples include 2 and 4 armed activated branched PEG spacers, although spacers with more arms, such as 8 or 12 armed activated branched PEG spacers also can be used. Branched activated PEG spacers (e.g., activated with maleimide) are commercially available (e.g., NOF Corporation, Tokyo, Japan).

In a preferred embodiment, the Tie 2 binding peptide monomer comprises a structure: A-B-C, wherein A comprises a Tie 2 binding peptide, B comprises a spacer and C comprises a multimerizing group, wherein C has affinity for D, a multimer agent comprising multiple binding sites for C. In a particularly preferred embodiment, the multimer agent D has four binding sites for the multimerizing group C such that a tetramer is formed when four Tie 2 binding peptide monomers, A-B-C, interact with the multimer agent D. A preferred multimerizing group, C, for use in creating tetramers is a biotin group. Preferred multimer agents, D, for use in creating tetramers are avidin, streptavidin and neutravidin. It is well known in the art that avidin, streptavidin and neutravidin have four binding sites for biotin and that biotin binds with high affinity to each of avidin, streptavidin and neutravidin. A preferred spacer, B, for use in a monomer of the structure A-B-C is a polyethylene glycol (PEG) spacer.

In another embodiment, the Tie 2 binding peptide monomer comprises a structure: A-B, wherein A comprises a Tie 2 binding peptide and B comprises a spacer, wherein the multimeric form is created by covalent linkage of multiple Tie 2 binding peptide monomers via the spacer B. A preferred spacer, B, for use in a monomer of the structure A-B is a polyethylene glycol (PEG) spacer.

In a particularly preferred embodiment, the invention provides a composition comprising a tetramer form of a Tie 2 binding peptide monomer, wherein the Tie 2 binding peptide monomer comprises a structure: A-B-C, wherein:

A comprises a Tie 2 binding peptide selected from a T7 peptide and a GA3 peptide;

B comprises a polyethylene glycol spacer; and

C comprises a biotin group, wherein four copies of A-B-C are associated with a tetramer agent, D, to create the tetramer form, the tetramer agent, D, being selected from the group consisting of avidin, streptavidin and neutravidin. A specific example of this embodiment is the compound Vasculotide (described in detail in the Example), in which A comprises a T7 peptide, B comprises a polyethylene glycol spacer and C comprises a biotin group, and wherein multimeric Vasculotide comprises avidin as the tetramer agent D.

In another aspect, the invention provides a composition comprising a Tie 2 binding peptide monomer, the Tie 2 binding peptide monomer comprising a structure A-B-C, wherein:

A comprises a Tie 2 binding peptide;

B comprises a spacer; and

C comprises a multimerizing group.

Preferably, the Tie 2 binding peptide, A, comprises a T7 peptide or a GA3 peptide. Alternatively, the Tie 2 binding peptide can comprises, for example, a T8 peptide, a T6 peptide or a T4 peptide. Preferably, the spacer, B, comprises a polyethylene glycol spacer. Preferably, the multimerizing group, C, comprises a biotin group.

In a preferred embodiment, the multimeric form of the invention comprises a peptide dimer, comprising: (a) a first peptide chain; (b) a second peptide chain; and (c) a linking moiety connecting said first and second peptide chains, wherein said peptide dimer binds to and activates the Tie 2 receptor. Preferably, the first peptide chain is a T7 peptide. Preferably, the second peptide chain is a T7 peptide. More preferably, both the first and second peptide chains are T7 peptides. Alternatively, the first and second peptide chains independently can be selected from the group consisting of a T7 peptide, a GA3 peptide, a T4 peptide, a T6 peptide and a T8 peptide, although preferably the first and second peptide chains are both the same type of peptide chain. Additional Tie 2 binding peptides that can be used are described in further detail above.

Preferably, the linking moiety comprises one or more water soluble polymers covalently bound to the first peptide chain and the second peptide chain. More preferably, the one or more water soluble polymers are linear polymers. In a preferred embodiment, the water soluble polymer is a polyethylene glycol (PEG) (e.g., a linear PEG molecule). Preferably, the PEG has a molecular weight of less than about 20,000 Daltons. More preferably, the linear PEG has a molecular weight in the range of about 3,000 Daltons to about 10,000 Daltons. In various embodiments, the linear PEG has a molecular weight of about 3,000 Daltons, about 3,400 Daltons, about 5,000 Daltons or about 10.000 Daltons. It is understood that in a given preparation of PEG, the molecular weights will typically vary among individual molecules. Some molecules will weight more, and some less, than the stated molecular weight. Such variation is generally reflected by use of the word "about" to describe the molecular weights of the PEG molecules.

As demonstrated in Example 11, T7-PEG dimers comprising PEG having a molecular weight of 10,000 Da exhibited effective activation of Tie 2 and downstream pathways (e.g, MAPK, AKT) in vivo, whereas T7-PEG dimers comprising a PEG having a molecular weight of 20,000 Da did not effectively activate Tie 2 or downstream pathways, indicating that the longer PEG linker resulted in a dimer in which the two peptide chains were spaced too far apart for optimal activation of Tie 2 and, thus, the shorter linkers may be preferably for optimal results. Accordingly, dimers utilizing a linear PEG linker having a molecular weight less than about 20,000 Da, more preferably having a molecular weight in the range of about 3,000 Daltons to about 10,000 Da, are preferred.

In another embodiment, the multimeric form of the invention comprises a peptide tetramer, comprising: (a) a first peptide chain; (b) a second peptide chain; (c) a third peptide chain; (d) a fourth peptide chain; and (e) a linking moiety connecting said first, second, third and fourth peptide chains, wherein said peptide tetramer binds to and activates the Tie 2 receptor. Preferably, the first, second, third and fourth peptide chains are T7 peptides. Alternatively, the first, second, third and fourth peptide chains independently can be selected from the group consisting of a T7 peptide, a GA3 peptide, a T4 peptide, a T6 peptide and a T8 peptide, although preferably the first, second, third and fourth peptide chains are all the same type of peptide chain. Additional Tie 2 binding peptides that can be used are described in further detail above.

Preferably, the linking moiety comprises one or more water soluble polymers covalently bound to the first, second, third and fourth peptide chains. More preferably, the one or more water soluble polymers are branched chain polymers. In a preferred embodiment, the water soluble polymer is a polyethylene glycol (PEG) (e.g., a branched chain PEG molecule). As demonstrated in Example 11, a T7-PEG tetramer utilizing a branched chain tetrameric PEG linker having a molecular weight of 20,000 Da was effective in activating Tie 2 and downstream pathways (e.g., MAPK, AKT) in vivo. Preferably, the branched PEG has a molecular weight in the range of about 3,000 Daltons to about 20,000 Daltons. In various embodiments, the branched PEG has a molecular weight of about 3,000 Daltons, about 3,400 Daltons, about 5,000 Daltons, about 10,000 Daltons or about 20,000 Daltons. It is understood that in a given preparation of PEG, the molecular weights will typically vary among individual molecules. Some molecules will weight more, and some less, than the stated molecular weight. Such variation is generally reflected by use of the word "about" to describe the molecular weights of the PEG molecules.

In the PEG-containing dimers, a single, preferably linear, PEG moiety is simultaneously attached to the termini (e.g., the N-termini) of both peptide chains of the peptide dimer. In the PEG containing tetramers, a single, branched chain PEG moiety is simultaneously attached to the termini (e.g., the N-termini) of the four peptide chains of the peptide tetramer. Such peptide dimers and tetramers are illustrated schematically in FIG. 6. To prepare the PEG-containing dimeric and tetrameric compounds described above, Tie 2 binding peptides can be reacted with activated PEG linkers (e.g., PEG dimaleimide for preparation of dimers, PEG tetramaleimide for preparation of tetramers) as described in detail in Example 9. Such activated PEG linkers (linear or branched chain) are commercially available (e.g., from NOF America Corporation).

In addition to the dimers and tetramers described above, the invention encompasses other multimeric forms comprising two or more Tie 2 binding peptides linked by a linking moiety, such as those containing three, five, six, seven, eight, nine, ten, eleven or twelve Tie 2 binding peptides covalently linked to a linking moiety, preferably a branched linking moiety, such as a branched chain PEG molecule. Such alternative multimeric forms can be prepared as described for the dimers and tetramers, using linker moieties having the appropriate number of reactive ends (e.g., six reactive ends for a multimer containing six peptide chains) and the appriate ratio of peptide to linker (e.g., 6:1 for a multimer containing six peptide chains).

While PEG linkers are preferred water soluble polymer linkers o f the invention, alternative water soluble polymer linkers include, but are not limited to, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, propropylene glycol homopolymers, polypropylene oxide/ethylene oxide copolymers, and polyoxyethylated polyols. For peptide dimers, preferably the polymer linker has a molecular weight of less than 20,000 Da and more preferably has a molecular weight of 10,000 Da. For peptide tetramers, preferably the polymer linker has a molecular weight of 20,000 Da.

In addition to water soluble polymers, other types of linking moieties known in the art can be used join the peptide chains in the multimers (e.g., two peptide chains in the dimer, four peptide chains in the tetramer). Non-limiting examples of additional suitable linker moieties that can be used to join multiple peptide chains to form multimers include those described in US Publication 20070104704 and US Publication 20070027074, the entire contents of both of which are expressly incorporated herein by reference.

In yet another aspect, the invention provides a composition comprising a Tie 2 binding peptide monomer, the Tie 2 binding peptide monomer comprising a structure A-B, wherein:

A comprises a Tie 2 binding peptide; and

B comprises a spacer.

Preferably, the Tie 2 binding peptide, A, comprises a T7 peptide or a GA3 peptide. Alternatively, the Tie 2 binding peptide can comprises, for example, a T8 peptide, a T6 peptide or a T4 peptide. Preferably, the spacer, B, comprises a polyethylene glycol spacer.

The invention also provides kits comprising one or more compositions of the invention, preferably packaged with instructions for use of the kit. For example, in a preferred embodiment, the invention provides a kit comprising a Tie 2 binding peptide monomer comprising the structure A-B-C, wherein A comprises a Tie 2 binding peptide;

B comprises a spacer; and

C comprises a multimerizing group;

packaged together with a multimer agent, D, wherein C has affinity for D, and wherein D comprises multiple binding sites for C. Preferred examples of A, B, C and D are as described previously herein. Preferably, the kit is packaged with instructions for creating a multimer form of the Tie 2 binding peptide monomer by combining the monomer composition with the multimer agents such that a multimeric form of the monomer is produced.

In another embodiment, the invention provides a kit comprising a Tie 2 binding peptide monomer comprising the structure A-B, wherein A comprises a Tie 2 binding peptide; and B comprises a spacer;

packaged together with instructions for creating a multimer form of the Tie 2 binding peptide monomer by multimerization through the spacer, B. Optionally, the kit may contain one or more reagents that facilitate multimerization through B. Preferred examples of A and B are as described previously herein.

II. Characteristic Properties of Multimeric Forms of Tie 2 Binding Peptide Monomers The multimeric forms of Tie 2 binding peptide monomers provided by the invention exhibit Tie 2 agonist activity. This Tie 2 agonist activity can be detected using indicators of Tie 2 activation that are well established in the art and that are described in detail in the Examples. For example, a multimeric form of the invention can stimulate Tie 2 phosphorylation (e.g., phosphorylation at amino acid residue Y992 of human Tie 2). Furthermore, a multimeric form of the invention can stimulate phosphorylation of a molecule in a downstream signalling pathway of Tie 2, such as phosphorylation of MAPK, AKT (e.g., phosphorylation at amino acid residue S473 of human AKT) and/or eNOS (e.g., phosphorylation at amino acid residue S1177 of eNOS). In particular embodiments, a multimeric form of the invention does not stimulate phosphorylation of focal adhesion kinase (FAK) (e.g., phosphorylation at amino acid reside Y397 of human FAK), which differentiates the multimeric form from native Ang 1, which has been shown to activate FAK by a Tie 2-independent manner. The ability of a multimeric form to stimulate phosphorylation of particular proteins can be determined used standard techniques well-known in the art, such as immunoblot assays of cell lysates treated with the multimeric form, as described in detail in Example 3.

In preferred embodiments, a multimeric form of the invention has demonstrable effects on endothelial cells. For example, a multimeric form of the invention preferably has at least one effect on endothelial cells selected from the group consisting of: stimulation of endothelial cell migration, stimulation of MMP2 release from endothelial cells and protection of endothelial cells from serum withdrawal-induced apoptosis. More preferably, a multimeric form of the invention has at least two of these effects on endothelial cells and even more preferably has all three of these effects on endothelial cells. The ability of a multimeric form to have any of these effects on endothelial cells can be determined using assays known in the art, such as a Boyden chamber assay to assess cell migration, a zymography assay to assess MMP2 release or a cell death ELISA assay to assess serum withdrawal induced apoptosis. Such assays are described in detail in Example 4.

In preferred embodiments, a multimeric form of the invention has demonstrable effects on angiogenesis, as measured in an in vitro or in vivo angiogenesis assay. A preferred assay is an in vivo Matrigel assay (described in detail in Example 5), in which growth factor reduced Matrigel is impregnated with the multimeric form and injected subcutaneously into a test animal. After a period of time (e.g., 14 days), the test animal can be treated with an agent that facilitates vessel identification and quantitation (e.g., FITC-lectin) and the Matrigel plug can be removed and examined for an angiogenic response. As demonstrated in Example 5, a multimeric form of the invention is capable of inducing a robust angiogenic response, as evidenced by large, well branched vessels that contain a continuum of small and large arterioles and venules and that stain positively for the myogenic support cell marker, Sma I. Significantly, the multimeric forms of the invention can stimulate an angiogenic response in an in vivo assay (e.g., Matrigel assay) that displays more organized branching patterns and less tortuosity that the angiogenic response stimulated by VEGF. Still further, preferred multimeric forms of the invention, when used in combination with VEGF, can decrease the level of vessel tortuosity that is seen with VEGF treatment alone.

In preferred embodiments, a multimeric form of the invention can stimulate wound healing in a subject when applied topically to a wound of the subject. The ability of the multimeric form to stimulate wound healing can be assessed in an animal model, such as the B6.Cg-m(+/+)Lepr(db)/J (db/db) strain of mouse, a diabetic strain of mouse that presents with impaired wound healing. An excisional wound can be made on the mouse, the multimeric form, incorporated into a topical formulation, can be applied to the wound and wound healing can be assessed as described in Example 6. Preferred multimeric forms of the invention can accelerate wound closure times and/or can promote increases in collagen deposition and neovascularization.

III. Preparation of Multimeric Forms of Tie 2 Binding Peptide Monomers

The preparation of a multimeric form of the invention typically involves at least two steps: first, preparation of the Tie 2 binding peptide monomer and second, multimerization of the monomer to create the multimer form.

The Tie 2 binding peptide contained within the monomer can be prepared by one of many methods known in the art for peptide synthesis, including but not limited to solid phase peptide synthesis (SPPS) and liquid phase peptide synthesis (LPPS). The two most common chemistries used in peptide synthesis are Fmoc and Boc; each chemistry has its own side chain protection characteristics that allow for selective deprotection of side chains for post synthesis modifications. For SPPS, a summary of many techniques may be found in J. M. Stewart and J. D. Young, *Solid Phase Peptide Synthesis*, W.H. Freeman Co. (San Francisco) 1963, and J. Meienhofer, *Hormonal Proteins and Peptides*, vol. 2, p. 46, Academic Press (New York), 1973. A preferred peptide synthesis method is Fmoc-SPPS, a recent summary of which can be found in W. Chan, *Fmoc Solid Phase Peptide Synthesis: A Practical Approach*, Oxford University Press (United Kingdom) 1999. Peptides can be synthesized using an automated peptide synthesizer, such as Applied Biosystems' ABI433A Peptide Synthesizer (Foster City, Calif., USA).

In addition to containing the amino acid sequence that interacts with the Tie 2 receptor, the Tie 2 binding peptide can be modified to contain one or more additional amino acid residues that function to facilitate further modification of the peptide. For example, an amino terminal cysteine residue can be added during synthesis to the Tie 2 binding peptide sequence to provide a reactive sulfhydryl group to allow for attachment of one or more additional chemical moieties via the sulfhydryl group. It will be apparent to the ordinarily skilled artisan that various other chemical modifications of the peptide can be performed to create a reactive group that can be used to link chemical moieties to the peptide. For example, the peptide can be modified during synthesis to contain an amino terminal lysine residue to provide a reactive primary amino group to allow for attachment of one or more additional chemical moieties via the primary amine group. Alternatively, the peptide can be modified during synthesis to contain an amino terminal aspartic acid or glutamic acid residue to provide a reactive carboxyl group to allow for attachment of one or more additional chemical moieties via the carboxyl group. Preferably, chemical modification of the peptide is carried out at the amino terminal or carboxy terminal end of the peptide so as to minimize any possible interference with the Tie 2 binding portion of the peptide.

As discussed herein, the Tie 2 binding peptide monomer can include other chemical moieties in addition to the Tie 2 binding peptide, such as a spacer moiety and/or a multimerizing group, which additional chemical moieties can be attached using chemical reactions well known in the art. For example, a Tie 2 binding peptide that contains a reactive sulfhydryl group (e.g., an amino terminal cysteine residue) can be reacted with a maleimide group that is linked to one or more additional chemical moieties of interest to thereby link the additional chemical moieties to the Tie 2 binding peptide. Nonlimiting examples of commercially available reagents that can be used to link a spacer group and a multimerizing group to a peptide having a reactive sulfhydryl group include maleimide-$PEO_2$-biotin and maleimide-$PEO_{11}$-biotin (Pierce Chemical, Rockford, Ill., USA). Nonlimiting examples of commercially available reagents that can be used to link a spacer group and a multimerizing group to a peptide having a reactive primary amine group include NHS-$PEO_4$-biotin, NHS-$PEO_{12}$-biotin and NHS-SS-biotin (Pierce Chemical, Rockford, Ill., USA). Nonlimiting examples of commercially available reagents that can be used to link a spacer group and a multimerizing group to a peptide having a reactive carboxyl group include Amine-$PEO_2$-biotin and biotin-PEO-LC-Amine (Pierce Chemical, Rockford, Ill., USA). Other examples of suitable reagents for linking a spacer-biotin reagent to a Tie 2 binding peptide via either a reactive sulfhydryl group, primary amine group or carboxyl group are set forth in subsection I above.

In a preferred embodiment, the invention provides a method of making a Tie 2 binding peptide monomer comprising a structure: A-B-C, wherein:

A comprises a Tie 2 binding peptide;
B comprises a polyethylene glycol spacer; and
C comprises a biotin group, the method comprising reacting a Tie 2 binding peptide comprising an amino terminal amino acid residue comprising a first reactive group with a reagent comprising the structure: second reactive group-B-C, wherein the first reactive group reacts with the second reactive group to form A-B-C. For example, the first reactive group can be a sulfhydryl group (e.g., the amino terminal amino acid residue of the peptide can be cysteine residue) and the second reactive group can be a maleimide group. Other suitable examples of first and second reactive groups are described above regarding suitable commercially available spacer reagents.

In another embodiment, the invention provides a method of making a Tie 2 binding peptide monomer comprising a structure: A-B, wherein:

A comprises a Tie 2 binding peptide; and
B comprises a polyethylene glycol spacer;

the method comprising reacting a Tie 2 binding peptide comprising an amino terminal amino acid residue comprising a first reactive group with a reagent comprising the structure: second reactive group-B to form A-B. For example, the first reactive group can be a sulfhydryl group (e.g., the amino terminal amino acid residue of the peptide can be cysteine residue) and the second reactive group can be a maleimide group. Other suitable examples of first and second reactive groups are described above regarding suitable commercially available spacer reagents.

To create the multimeric forms of the Tie 2 binding peptide monomers of the invention, multiple copies of the monomers are linked together to thereby multimerize the monomers. Multimerization can be accomplished by one of several possible methods. For example, for monomers that comprise a multimerizing group (e.g., monomers of the structure A-B-C), the monomers can be combined with a multimer agent that has affinity for the multimerizing group and that has multiple binding sites for the multimerizing group. Depending on the number of binding sites that the multimer agent has, the ratio of monomer to multimer agent can be adjusted accordingly. For example, when the multimerizing group is biotin and the multimer agent is avidin, streptavidin or neutravidin (each of which have four binding sites for biotin), the ratio of monomer to multimer agent can be selected as 4:1. Accordingly, the invention provides a preferred method of making a tetramer form of a Tie 2 binding peptide monomer of the structure A-B-C, wherein A is a Tie 2 binding peptide, B is a spacer and C is biotin, the method comprising combining the Tie 2 binding peptide monomer, A-B-C, with a tetramer agent, D, at a 4:1 ratio, the tetramer agent, D, being selected from the group consisting of avidin, streptavidin and neutravidin.

In an alternative embodiment, differing ratios of monomer (e.g., A-B-C) and multimer agents (e.g., D) can be combined to create multimers having different numbers of monomer units. Thus, when the multimer agent is a tetramer, a 4:1 ratio of monomer to multimer agent can be used to achieve tetrameric multimers, but lower ratios also can be used to achieve trimers or dimers. More specifically, a 3:1 ratio of monomers to multimer agent can be used to achieve trimers and a 2:1 ratio of monomer to multimer agent can be used to achieve dimers. Preferably, after the monomers and multimer agent are combined, one or more purification steps are carried out to purify the desired multimeric form and/or to remove unbound monomers. Nonlimiting examples of purification techniques that can be used to isolate the desired multimeric species include HPLC, size exclusion chromatography and avidin agarose chromatography (to remove unbound monomers linked to a biotin multimerizing group).

For monomers having a structure A-B, wherein A is a Tie 2 binding peptide and B is a spacer, multimerization can be accomplished by covalent linkage or noncovalent association of multiple copies of the monomer through the spacer B. For example, branched activated PEG spacers (commercially available from NOF Corporation, Tokyo, Japan) can be reacted with multiple copies of the monomer to create the multimeric structure. Numerous suitable reactive groups are available with which the branched arm spacer can be activated, including but not limited to maleimide, amine, glutaryl-NHS, carboxymethyl-NHS, carbonate and aldehyde. Following reaction of the monomer with the branched arm spacer, preferably one or more purification steps are carried out to purify the desired multimeric form and/or to remove unbound monomers, as described above.

IV. Methods of Detecting a Composition Comprising a Tie 2 Binding Peptide

In another aspect, the invention provide a method of detecting the compositions of the invention comprising a multimeric form of a Tie 2 binding peptide. In the detection method, a composition of the invention is contacted with a monoclonal antibody that specifically binds to the Tie 2 binding peptide contained within the multimeric form such that the Tie 2 binding peptide is detected. Specific formats of detection assay that are known in the art that are applicable to the detection of the Tie 2 binding peptide include, for example, enzyme linked immunosorbent assay (ELISA) and radioimmunoassay (RIA). Preferred monoclonal antibodies for use in the assays are those that specifically bind to the T7 peptide contained within multimeric forms of the T7 peptide, such as those described in Example 12. Monoclonal antibodies that bind to the Tie 2 binding peptide (e.g., T7) can be prepared by standard techniques. Assessment of the binding of the monoclonal antibody to the Tie 2 binding peptide also can be performed by standard techniques, such as ELISA, RIA, dot blot analysis, immunoblot analysis, immunoprecipitation and the like, as described further in Example 12.

The invention also provides monoclonal antibody compositions that specifically bind to the T7 peptide. Non-limiting examples of such monoclonal antibodies include the antibodies secreted by the hybridoma clones 2C11, 13D4, 3E4 and 4H6 described further in Example 12.

V. Pharmaceutical Compositions and Administration Thereof

Another aspect of the invention pertains to pharmaceutical compositions comprising the multimeric forms of the Tie 2 binding peptide monomers of the invention. The pharmaceutical compositions typically include the multimeric form of the Tie 2 binding peptide monomer and a pharmaceutically acceptable carrier. Pharmaceutically acceptable carriers can be selected to be suitable for the desired route of administration. For example, in one embodiment, the pharmaceutically acceptable carrier is suitable for topical administration. A non-limiting example of a suitable carrier for topical administration is IntraSite Gel (commercially available from Smith & Nephew). In another embodiment, the pharmaceutically acceptable carrier is suitable for systemic administration. A non-limiting example of a suitable carrier for systemic (e.g., intravenous) administration is phosphate buffered saline (PBS).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for topical administration or for intravenous, intramuscular, subcutaneous, parenteral, spinal or epidermal administration (e.g., by injection or infusion). Depending on the route of administration, the active compound, i.e., multimeric form of the Tie 2 binding monomer, may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects (see e.g., Berge, S. M. et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain, for example, preservatives, wetting agents, emulsifying agents and/or dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Therapeutic compositions typically must be sterile and stable under the conditions of manufacture and storage. Sterile injectable solutions can be prepared by incorporating the active compound in the required amount in an appropriate solvent with one or a combination of ingredients enumerated above, as required, followed by sterilization microfiltration. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For systemic administration of the multimeric form of the Tie 2 binding peptide monomer, the dosage typically ranges from about 0.0001 to 100 mg/kg, and more usually 0.001 to 5 mg/kg, of the host body weight. For example dosages can be 1 µg/kg, 5 µg/kg, 50 µg/kg, 0.1 mg/kg, 0.3 mg/kg body weight, 1 mg/kg body weight, 3 mg/kg body weight, 5 mg/kg body weight or 10 mg/kg body weight or within the range of 0.01-1 mg/kg. For topical administration, exemplary dosage ranges are from about 5 µg/ml to about 5 mg/kg, more preferably 50 µg/kg to 2 mg/kg, such as 1 mg/kg.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A "therapeutically effective dosage" of the multimeric form of the Tie 2 binding peptide monomer of the invention preferably results in increased angiogenesis, stimulation of wound healing or both. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for the multimeric forms of the invention include non-parenteral routes, including topical, epidermal or mucosal routes of administration, for example, intranasally, orally, vaginally, rectally, sublingually or topically. Alternatively, other preferred routes of administration include parental routes, including intravenous, intramuscular, intradermal, intraperitoneal, subcutaneous, spinal, intraarterial, intrathecal, intracapsular, intraorbital, intracardiac, transtracheal, subcuticular, intraarticular, subcapsular, subarachnoid, intraspinal, epidural and intrasternal injection and infusion.

In certain embodiments, the multimeric forms of the Tie 2 binding peptide monomers of the invention can be administered in combination with other therapeutic agents, such as other agents that promote angiogenesis and/or stimulate wound healing. Non-limiting examples of other agents with which the multimeric forms of the invention can be combined include VEGF, PDGF, G-CSF, recombinant human erythropoietin, bFGF and placental growth factor (PLGF).

VI. Methods of Using Multimeric Forms of Tie 2 Binding Peptide Monomers

Another aspect of the invention pertains to methods of using the multimeric forms of the Tie 2 binding peptide monomers of the invention. As discussed herein, the multimeric forms have Tie 2 agonist activity. Accordingly, the multimeric forms can be used to activate the Tie 2 receptor, either in vitro or in vivo. Thus, in one embodiment, the invention provides a method of activating a Tie 2 receptor comprising contacting the Tie 2 receptor with the multimeric form of the Tie 2 binding peptide monomer such that the Tie 2 receptor is activated. Activation of the Tie 2 receptor can be evidenced by any of numerous possible indicators of Tie 2 activation well established in the art, including but not limited to the various in vitro and in vivo assays described in detail in the Examples.

In one embodiment, for example, wherein activation of the Tie 2 receptor is evidenced by phosphorylation of residue tyrosine 992 (Y992) of the Tie 2 receptor. In another embodiment, for example, activation of the Tie 2 receptor is evidenced by phosphorylation of MAPK, AKT or eNOS.

Since the multimeric forms of the invention have angiogenic activity, the invention also provides a method of stimulating angiogenesis at a site in a subject, wherein the method comprises contacting the site with the multimeric form of the Tie 2 binding peptide monomer such that angiogenesis is stimulated at the site in the subject. In one embodiment, the multimeric form is contacted with the site by topical administration of the multimeric form. In another embodiment, the multimeric form is contacted with the site by systemic administration of the multimeric form. Angiogenesis can be confirmed by the presence of one or more well established characteristics of angiogenesis. In a preferred embodiment, angiogenesis stimulated by the multimeric form is characterized by at least one of the following properties:

a) recruitment of perivascular support cells;
  b) non-leakiness of vessels; and
  c) well-defined arborization.

Recruitment of perivascular support cells can be demonstrated by detection of a marker of smooth muscle cells, for example by immunostaining with an antibody against smooth muscle actin 1 (Sma 1). Non-leakiness of vessels can be assessed using vessel permeability assays established in the art, including in vitro and/or in vivo assays. A non-limiting example of an in vivo vessel permeability assay is the Miles assay using either Evan's Blue or FITC albumin. As used herein, vessels are to be considered "non-leaky" if the degree of permeability of the vessels is less than the degree of permeability of vessels whose growth was stimulated by VEGF treatment. Well-defined arborization can be demonstrated, for example, by imaging of newly formed vessels and quantification of number of vessels and number of nodes in a particular image field (see Example 5 for a more detailed description). Well-defined arborization is indicated by, for example, significant and organized branching of the vessels, such as angiogenesis in which the ratio of the number of vessels to the number of nodes is 1.0:0.5, more preferably 1.0:0.7 or even more preferably 1.0:1.0. Furthermore, the flow dynamics of neovessels can be assessed using micro Doppler ultrasound.

In the method for stimulating angiogenesis, the site can be contacted with the multimer form alone or, alternatively, the site can be contacted with one or more additional angiogenic agents. Thus, in another embodiment, the angiogenesis method further comprises contacting the site in the subject with a second angiogenic agent. Non-limiting examples of additional angiogenic agents that can be used in combination with the multimeric forms of the invention include VEGF, PDGF, G-CSF, recombinant human erythropoietin, bFGF and placental growth factor (PLGF). As demonstrated herein, a multimeric form of the invention, when used in combination with VEGF, has been shown to reduce the vessel tortuosity and vascular permeability seen when VEGF is used alone to stimulate angiogenesis. Thus, in a preferred angiogenesis method of the invention, a multimeric form of the invention is used in combination with VEGF.

Given the ability of the multimeric forms of the invention to stimulate angiogenesis, the multimeric forms can be used in a variety of clinical situations in which promotion of angiogenesis is desirable. Non-limiting examples of such indications include vascularization of regenerative tissues, ischemic limb disease, cerebral ischemia, conditions of vascular inflammation including arteriosclerosis, avascular necrosis, stimulation of hair growth and erectile dysfunction.

Moreover, given the ability of the multimeric forms to reduce vascular permeability induced by other agents such as VEGF, the multimeric forms can be used clinically to counteract vascular permeability induced by, for example, VEGF, radiation, a pathogen or other clinical event (e.g., stroke). The ability of Ang 1 to protect vasculature against leakage and/or counteract endothelial permeability induced by other agents has been reported (see e.g., Thurston, G et al. (1999) *Science* 286:2511-2514; Thurston, G. et al. (2000) *Nat. Med.* 6:460-463; Pizurki, L. et al. (2003) *Br. J. Pharmacol.* 139:329-336; Jho, D. et al. (2005) *Circ. Res.* 96:1282-1290). Moreover, Ang 1 has been reported to reduce cerebral blood vessel leakage and promote stabilization of angiogenic vessels in experimental stroke models (Zhang, Z. G. et al. (2002) *Neurosci.* 113:683-687; Zacharek, A. et al. (2006) *Neurosci. Lett.* 404: 28-32), to inhibit breakdown of the blood-retinal barrier (Nambu, H. et al. (2004) *Gene Therap.* 11:865-873) and to inhibit retinal detachment in a model of proliferative retinopathy (Nambu, H. et al. (2005) *J. Cell. Physiol.* 204:227-235). In view of the demonstrated effects of the multimeric forms of the invention in decreasing vascular permeability, another aspect the invention pertains to a method of decreasing vascular permeability at a site of leaky vessels, the method comprising contacting the site of leaky vessels with a multimeric form of a Tie 2 binding peptide monomer of the invention such that vascular permeability is decreased. Such a method can be used in a variety of clinical situations, non-limiting examples of which include stroke, macular degeneration, macular edema, lymph edema, breakdown of the blood-retinal barrier, breakdown of the blood-brain barrier (e.g., during chemotherapeutic treatment) and normalization of tumor vasculature to facilitate drug delivery and increase radiation sensitivity.

The multimeric forms of the invention also have been shown to have a protective effect on endothelial cells, e.g., by inhibiting apoptosis of endothelial cells. The ability of a Tie 2 agonist to protect endothelial cells in renal vasculature has been reported to ameliorate renal fibrosis in an experimental model (Kim, W. et al. (2006) *J. Am. Soc. Nephrol.* 17:2474-2483). In view of the demonstrated effects of the multimeric forms of the invention in protecting endothelial cells, another aspect the invention pertains to a method of protecting endothelial cells, the method comprising contacting the endothelial cells with a multimeric form of a Tie 2 binding peptide monomer of the invention such that the endothelial cells are protected. Such a method can be used in a variety of clinical situations, non-limiting examples of which include kidney fibrosis, stroke, macular degeneration and diabetic complications (e.g., in the kidney, eye, skin and/or limbs).

The multimeric forms of the invention also have been shown to be effective in stimulating wound healing. Accordingly, in still another aspect, the invention provides a method of stimulating healing of a wound in a subject, the method comprising contacting the wound with a multimeric form of a Tie 2 binding peptide monomer of the invention such that healing of the wound is stimulated in the subject. In one embodiment, the multimeric form is contacted with the wound by topical administration of the multimeric form. In another embodiment, the multimeric form is contacted with the wound by systemic administration of the multimeric form. Stimulation of wound healing can be evidenced by, for example, accelerated wound closure time as compared to wound healing in the absence of the multimeric form, increased granulation tissue at the wound site as compared to no treatment with the multimeric form and/or enhanced neovascularization of the wound as compared to no treatment with the multimeric form.

In a preferred embodiment, the method of stimulating healing of wound is used in the treatment of a diabetic ulcer. Currently, there are 16 million people with diabetes in the U.S., with 798,000 new cases reported annually and a prevalence of approximately 6% of the population. Estimates report that 10-15% of diabetics will go on to develop foot ulcers, of which 14-20% will require amputation. Foot ulceration is the precursor to approximately 85% of lower extremity amputations. As demonstrated herein, a multimeric form of the invention can stimulate wound healing in an animal model of diabetic ulcers when the multimeric form is topically applied to the wound (see Example 6).

In other embodiments, the method of the invention for stimulating healing of a wound can be used in a variety of clinical situations involving wounds, including but not limited to decubitus ulcers, pressure ulcers, surgical incisions, traumatic tissue injuries, burns and skin grafts.

The multimeric forms of the invention also can be incorporated into a biomaterial that then can be implanted at a site in a subject to thereby provide the effects of the multimeric form at that site. Biomaterials that provide a matrix or scaffold are suitable for use. The multimeric form can be incorporated alone or in combination with one or more additional agents, such as VEGF, PDGF, G-CSF, recombinant human erythropoietin, bFGF and placental growth factor (PLGF). Non-limiting examples of suitable biomaterials include Matrigel, skin substitutes and cross-linked glycosaminoglycan hydrogels (e.g., as described in Riley, C. M. et al. (2006) *J. Biomaterials* 27:5935-5943). Accordingly, another aspect of the invention pertains to a biomaterial composition into which is incorporated a multimeric form of the invention, alone or in combination with one or more additional agents. A packaged material that comprises the biomaterial is also encompassed by the invention. The packaged material can be labeled for use of the biomaterial.

Various aspects and embodiments of the present invention are further described by way of the following Examples. The Examples are offered by way of illustration and not by way of limitation. The contents of all figures and all references, patents and published patent applications cited throughout this application are expressly incorporated herein by reference.

EXAMPLES

Example 1

Preparation of a Tetrameric Tie 2 Binding Peptide, Vasculotide

In this example, a tetrameric form of a 7mer peptide known to bind Tie 2 was prepared, using a biotin-avidin system to cluster the peptide as a tetramer. The peptide, referred to as T7, was previously described in Tournaire R. et al. (2004) *EMBO Reports* 5:262-267 and has an amino acid sequence of His-His-His-Arg-His-Ser-Phe (SEQ ID NO: 1).

The peptide was synthesized using Fmoc Solid Phase Peptide Synthesis, a summary of which synthesis method can be found in W. Chan, *Fmoc Solid Phase Peptide Synthesis: A Practical Approach*, Oxford University Press (UK), 1999. The peptide was synthesized using Applied Biosystems' ABI433A Peptide Synthesizer (Foster City, Calif., USA) using manufacturer's instructions with a few modifications. The modifications were: 1) coupling time was extended to 17.5 minutes and 2) HBTU was substituted by HATU. The resin used was Wang resin. To create a free sulfhydryl group on the peptide for further modification, an amino terminal cysteine residue was added to the peptide such that the final sequence of the peptide was Cys-His-His-His-Arg-His-Ser-Phe (SEQ ID NO: 2). The protection groups for the side chain residue were: Cys-(tBu), His-(Trt), Arg-(Pbf), Ser-(tBu). Amino acid derivatives used here were the L-form to mimic the natural folding conformation in mammalian cells. The cleavage cocktail used to cleave T7 peptide off the solid phase resin support contained: 90% Trifluoro acetic acid (TFA), 8% TIPS, 2% EDT. The cleavage was performed under nitrogen gas for 3 hours. The cleavage cocktail and the resin mixture were separated by means of Kimax Fritted funnel. T7 peptide was then precipitated with cold ether and centrifuged at 2700×g for 5 min at 4° C. The pellet was washed for a total of four times with cold ether. Each wash was carried out by 30 seconds vortexing, and 5 min centrifugation at 2700×g at 4° C. Finally, T7 peptide pellet was dried under nitrogen gas.

To create the tetramer, the T7 peptide first was modified by addition of a 29 angstrom biotinylated polyethylene glycol (PEG)-maleimide moiety, which is illustrated schematically in FIG. 1A. Biotin was conjugated to the T7 peptide by using EZ-link-PEO-maleimide-biotin (Pierce's catalog number 21901) according to the manufacturer's instruction. 20 mg of T7 peptide was dissolved in 5 mL of conjugation buffer (0.001 M EDTA, 0.2M phosphate buffer, pH 7.4) in a 15 mL tube. 10 mg EZ-link-PEO-maleimide-biotin was dissolved in 1 mL conjugation buffer, then was added into the T7 peptide solution and mixed by 5 seconds vortexing. The mixture was wrapped in foil and incubated at between 20-25° C. for four hours, then was stored in −20° C. until HPLC purification.

The T7-biotin product in the above reaction mixture was purified using reverse phase HPLC under the following conditions:

Column: Agilent Zorbax Extended-C18 (cat#770450-902), 4.6 mm (inner diameter)×250 mm (length), 5 micron particle, 80 A pore size Mobile Phase:

A: 20 mM Ammonium hydroxide (0.701 g/L) in distilled water.

B: 20 mM Ammonium hydroxide (0.701 g/L) in 90% methanol 10% distilled water.

Detection: UV 215 and 280 nm

Column was equilibrated in 90% mobile phase A for 15 minutes at flow rate 1 ml per minute. 200 microliter of the above peptide-biotin conjugation reaction mixture was injected at time zero according to the following flow scheme:

| Time | flow rate | percentage of B (all steps were isocratic) |
| --- | --- | --- |
| 0 minute | 0.2 mL/min | 10% |
| 5 minute | 0.5 mL/min | 10% |
| 10 minute | 1 mL/min | 33.1% |
| 30 minute | 1 mL/min | 33.2% |
| 45 minute | 1 mL/min | 33.3% |
| 60 minute | 1 mL/min | 33.4% |
| 70 minute | 1 mL/min | 0% |

The eluent were collected in a tube for every one minute. Isocratic elution of T7-biotin achieved at 33.3% of mobile phase B at retention time of 49 minutes. This fraction was verified by mass spectrometry (MS) to contain a parent ion with m/z=1585.69 (singly protonated monoisotopic peak). The theoretical m/z of the expected product is 1585.6894.

Post synthesis clustering of this biotinylated peptide-PEG, referred to hence forth as Vasculotide, with avidin in a 4:1 ratio (Vasculotide:avidin) gave rise to an obligate tetrameric compound.

Example 2

Characterization of the Tie 2 Binding of Vasculotide

In this example, the ability of Vasculotide to bind the Tie 2 receptor, despite the engineered modifications, was tested using an in vitro pull down assay. In the pull down assay, a cell lysate of EaHy926 endothelial cells (which express high levels of Tie 2) was prepared in Phospho Lipase Cγ lysis buffer (50 mM Hepes buffer pH 7.5, 150 mM NaCl, 10% glycerol, 1% Triton X-100, 1.5 mM $MgCl_2$, 1.0 mM EGTA, 10 mM NaPPi, 100 nM NaF, 2 mM $Na_3VO_4$, 1× aprotinin, 1× leupeptin and 1×PMSF). The whole cell lysate was mixed with either unclustered biotinylated Vasculotide or biotinylated irrelevant peptide. The biotinylated peptides then were isolated with avidin agarose and subsequently tested for their ability to precipitate Tie 2 via standard immunoblot analysis using anti-Tie 2 antibody.

Figure 1B:
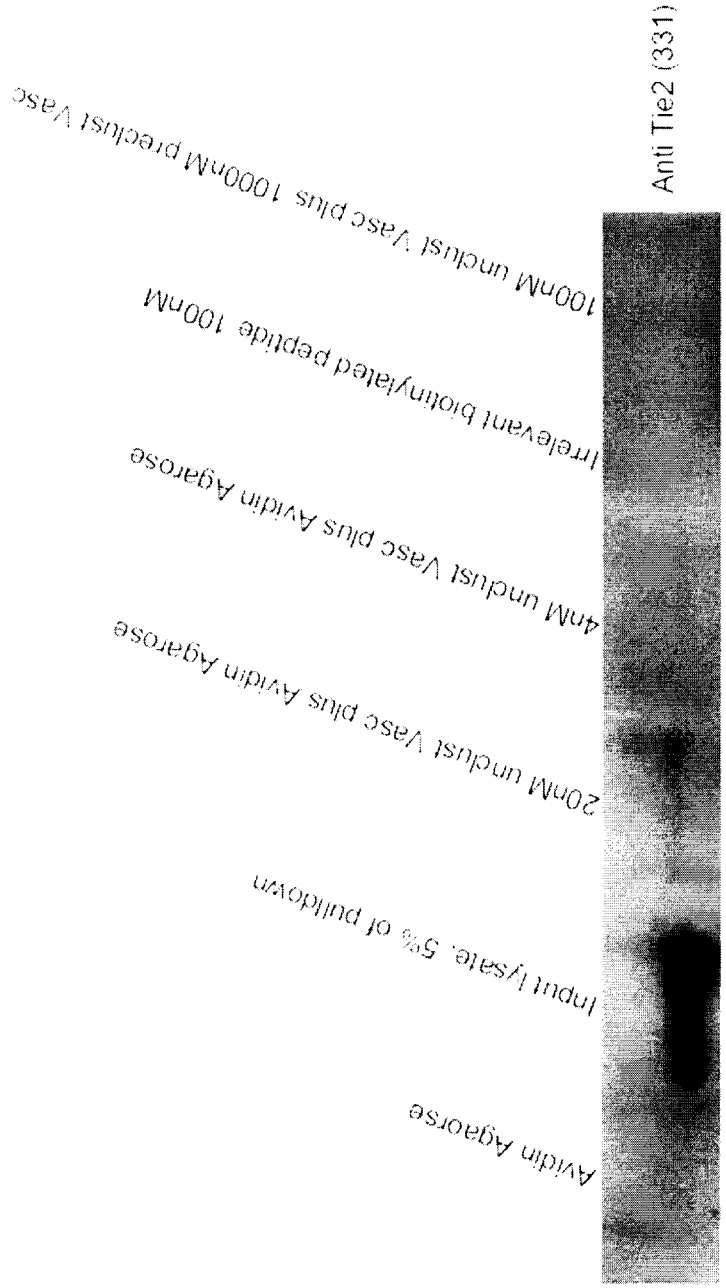
FIG. 1B is an immunoblot of an in vitro pull down assay, showing that unclustered Vasculotide, but not irrelevant biotinylated peptide, specifically binds Tie-2 in this assay.

The results of the immunoblot are shown in FIG. 1B. The results demonstrated that, when purified using avidin agarose resin, Vasculotide but not irrelevant biotinylated peptide was able to precipitate Tie 2. Addition of a ten fold excess of Vasculotide preclustered with soluble avidin was able to compete for available Tie 2 and was able to abolish this interaction (FIG. 1B, final lane).

Example 3

Characterization of the Tie 2 Activation by Vasculotide

Having established that Vasculotide was able to bind Tie 2 (see Example 2), the ability of Vasculotide, when clustered with avidin in a 4:1 ratio (Vasculotide:avidin), to activate the Tie 2 receptor was tested by examining several well established downstream signalling pathways in human umbilical vein endothelial cells (HUVEC) (Cambrex, N.J.). Such signalling pathways are described in, for example, Kim, I. et al. (2000) *Circ. Res.* 9:952-959; Fujikawa, K. et al. (1999) *Exp. Cell. Res.* 2:663-672; Babaei, S. et al. (2003) *Am. J. Pathol.* 6:1927-1936.

HUVEC were grown on 6-well or 10 cm plates (Nunc) coated with gelatin (Sigma). HUVEC were cultured in F12 growth medium containing 10% fetal bovine serum (FBS), 0.1 mg/ml heparin sulphate, 1× penicillin, 1× streptomycin, 1× glutamine, VEGF 10 ng/ml, EGF 10 ng/ml, bFGF 5 ng/ml. All HUVEC were used between passage 3-9.

HUVEC were stimulated with one of either Ang 1 (R&D Systems), Vasculotide, avidin or clustered Vasculotide (preclustered with a 4:1 molar ratio of peptide:avidin in PBS for 2 hours at 4° C.) at various doses. Stimulations with Vasculotide were performed in full serum containing growth media for 15 minutes unless otherwise indicated. Cell lysate preparations and immunoblot analysis were performed by standard methods. Antibodies used for immunoblotting (in this and/or subsequent Examples) were monoclonal anti Tie 2 (Pharminogen), polyclonal anti pY992 Tie 2, (Cell Signaling Technology), polyclonal anti MAPK (Cell Signaling Technology), monoclonal anti phospho MAPK (Cell Signaling Technology), polyclonal anti AKT (Cell Signaling Technology), polyclonal anti pS473 AKT (Cell Signaling Technology), monoclonal anti pS1177 eNOS (BD Biosciences), polyclonal anti pY397 FAK (Biosource), polyclonal anti FAK (Santa Cruz), polyclonal anti smooth muscle actin-Cy3 direct conjugate (Dako), polyclonal anti PECAM (Pharminogen) and polyclonal anti smooth muscle actin (Sigma).

Figure 1C:
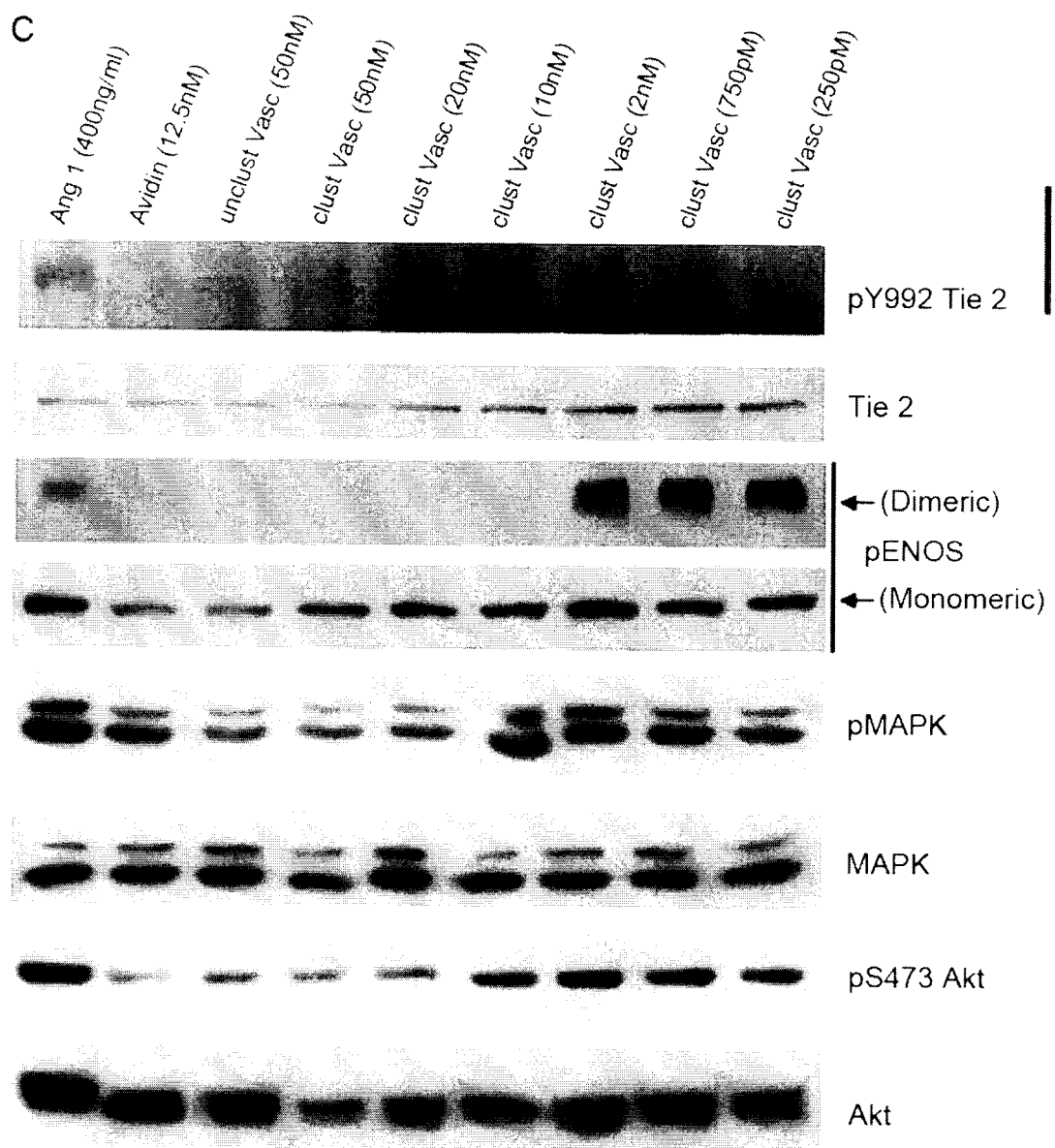
FIG. 1C is an immunoblot analysis of lysates from HUVECs stimulated with Ang 1, avidin, unclustered Vasculotide or clustered Vasculotide at various doses, showing that treatment with clustered Vasculotide results in activation of Tie 2 (Tek) and downstream signalling proteins eNOS, MAPK and AKT.

The results of the immunoblot analysis are shown in FIG. 1C. The immunoblot analysis of whole cell lysates revealed that clustered Vasculotide activates Tie 2 (pY992 Tie 2) at concentrations ranging from 20 nM to 750 pM, with 5-10 nM appearing optimal. Significantly, only when preclustered with avidin was Vasculotide able to stimulate Tie 2 phosphorylation (see avidin alone and unclustered Vasculotide). Coincident with receptor activation, phosphorylation of several known Tie 2-responsive proteins including MAPK, AKT and eNOS, was observed.

Figure 1D:
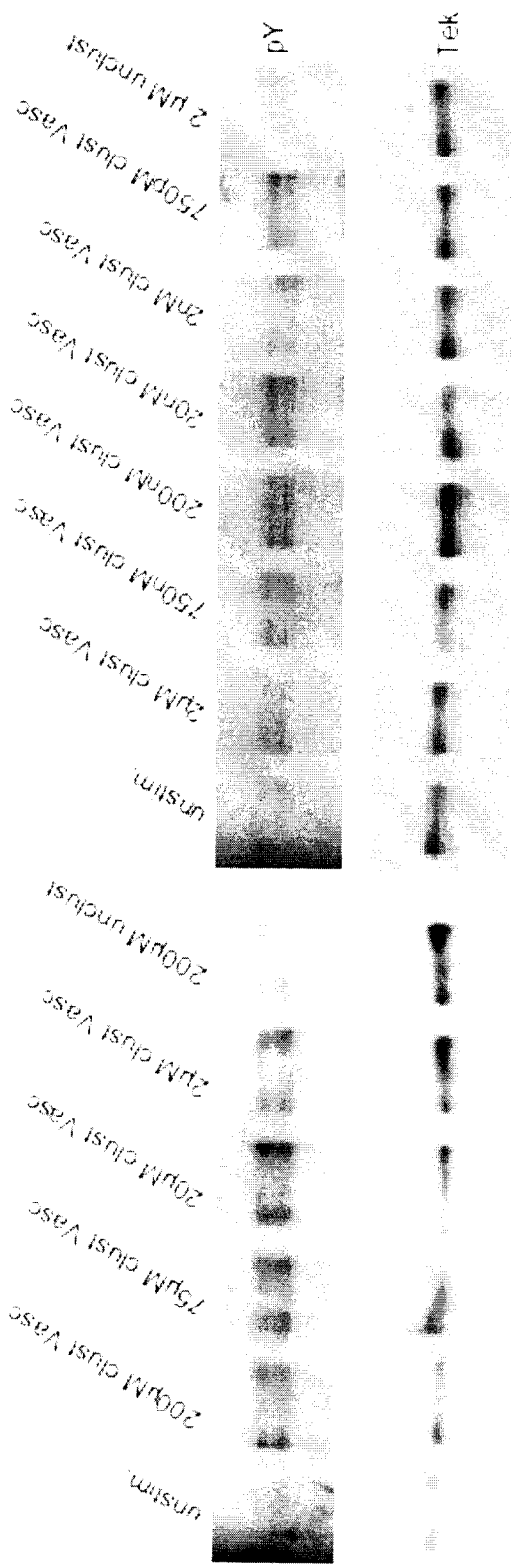
FIG. 1D is a dose analysis immunoblot of lysates from Eahy926 ECs stimulated with unclustered Vasculotide or clustered Vasculotide, showing that clustered Vasculotide activates Tie 2 receptor phosphorylation at concentrations ranging from 200 µM to 750 pM.

Paradoxically, high concentrations of clustered Vasculotide are not capable of activating Tie 2 receptor activity in HUVEC (see clustered Vasculotide 50 nM). It was hypothesized that this was due to the fact that high ratios of clustered Vasculotide:Tie 2 would decrease receptor clustering. To test this hypothesis, Eahy926 EC's, which express much higher levels of Tie 2, were utilized. For immunoblot analysis, Tie 2 was immunoprecipitated from the Eahy926 cells with monoclonal anti Tie 2 (Pharmingen, clone 33.1) and protein G sepharose (Amersham) and monoclonal anti pY (Upstate Biotechnology, clone 4G10), according to standard techniques. The results of this immunoblot are shown in FIG. 1D. Using this cell line, specific activation of the Tie 2 receptor at concentrations ranging from 200 μM to 750 pM was demonstrated, suggesting that the ratio of clustered Vasculotide:Tie 2 is critical for activation.

Figure 1E:
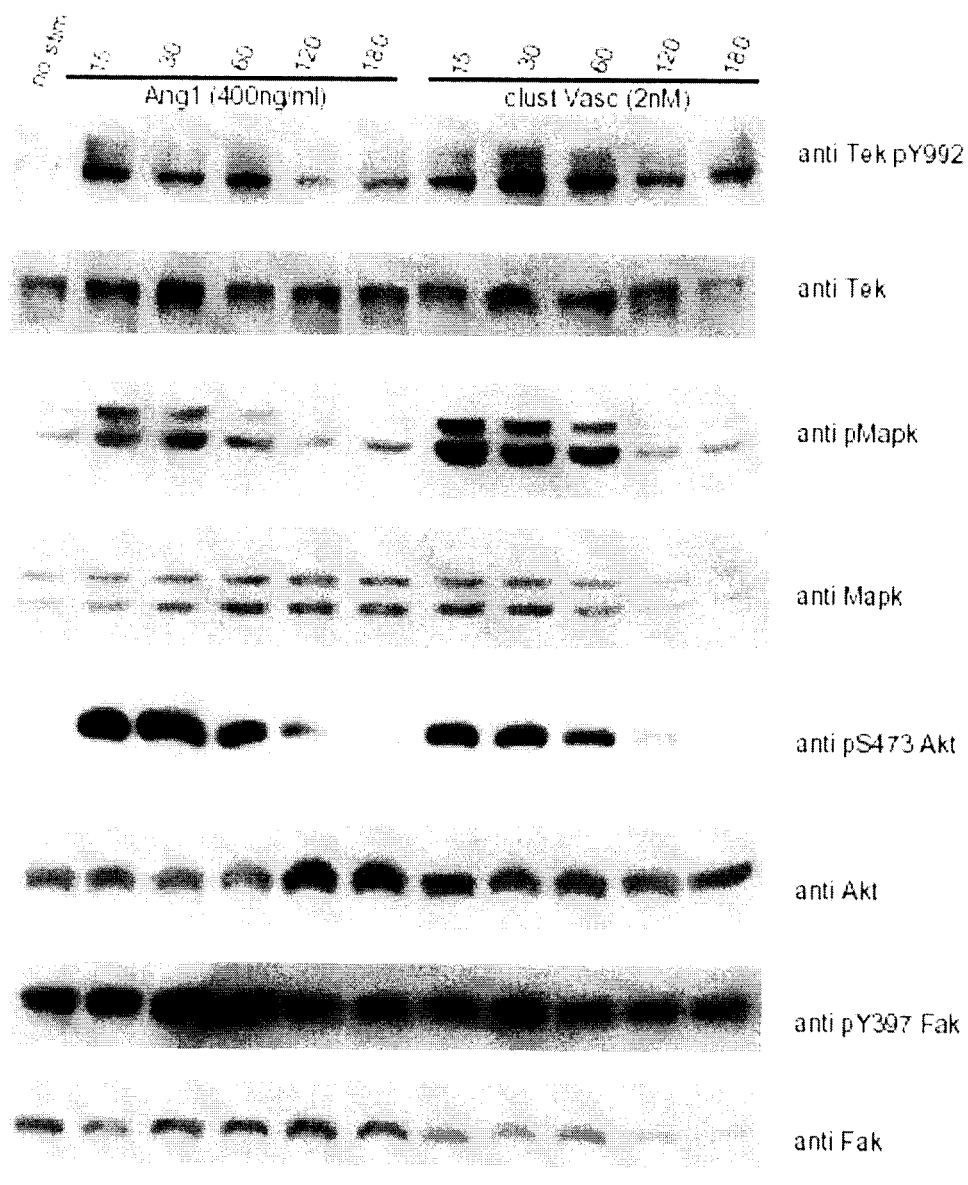
FIG. 1E is an immunoblot analysis of the activation kinetics of Tie 2 activation in HUVECs stimulated with Ang 1 or clustered Vasculotide for various times, showing that clustered Vasculotide activates Tie 2, AKT and MAPK, but not FAK, in HUVECs, with activation kinetics that closely mimic that of recombinant Ang 1.

To examine Tie 2 activation kinetics, HUVEC were stimulated with native Ang 1 or clustered Vasculotide for various times. Stimulation was performed in 10% FBS. The results are shown in FIG. 1E. Low concentration clustered Vasculotide (2 nM) compared favorably to Ang 1 (400 ng/ml) stimulation in its ability to activate Tie 2 phosphorylation. Overall, activation of the receptor by either Ang 1 or clustered Vasculotide followed a very similar time course with phosphorylation returning to almost basal levels sometime after 2 hours. Again, marked increases in pMAPK and pAKT were observed.

Previously, Ang 1 has been shown to activate focal adhesion kinase (FAK) in a Tie 2 independent manner through direct engagement of αVβ1 integrin (Hu, B. et al. (2006) *Cancer. Res.* 2:775-783; Kim, I et al. (2000) *Circ. Res.* 9:952-959; Dallabrida, S. et al. (2005) *Circ. Res.* 4:8-24). To test whether clustered Vasculotide was capable of activating this arm of the Ang 1 signalling cascade, the activation of FAK was examined, the results of which are also shown in FIG. 1E (bottom panel). As previously reported, Ang 1 time dependently activated FAK, whereas clustered Vasculotide had no significant effect. These results are suggestive of a more direct role for Vasculotide in eliciting Tie 2-specific signalling.

To more formally address the specificity of clustered Vasculotide for the Tie 2 receptor, reconstitution experiments were performed in Cos 1 fibroblast cells and C166 EC's, both of which are phenotypically null for Tie 2. Cos 1 and C166 cells (ATCC) were maintained on 10-cm-diameter plates (Nunc) in Dulbecco's modified Eagle's medium (DMEM) supplemented with 10% (FBS), 1× penicillin, 1× streptomycin, and 200 mM L-glutamine (all Gibco BRL) in a 5% $CO_2$ incubator at 37° C. Cos1 or C166 cells were infected (MOI 30) overnight with adenoviruses encoding one of either enhanced green fluorescent protein (EGFP) or Tie 2. Infection efficiency was confirmed by epifluorescence (EGFP), or by immunoblot (Tie 2).

Figure 1F:
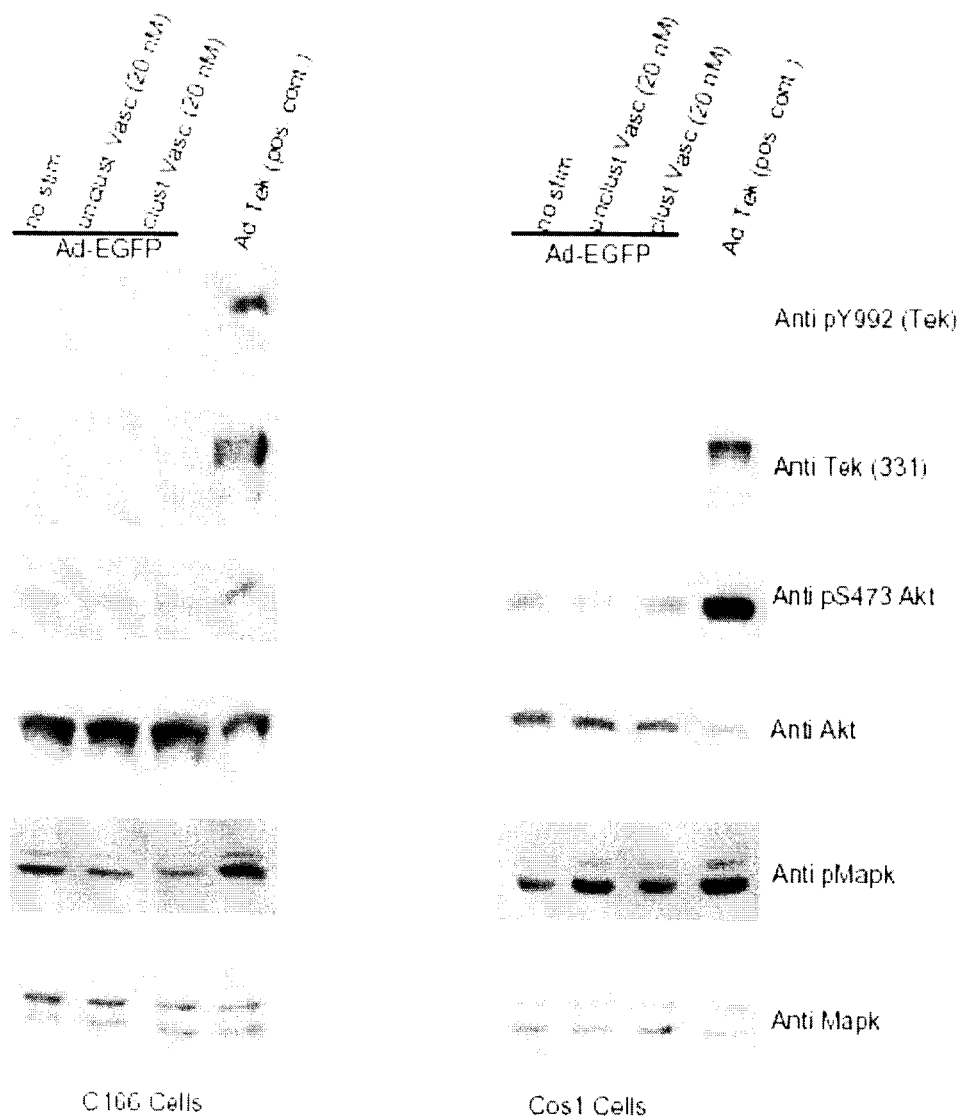
FIG. 1F is an immunoblot analysis of lysates from C166 cells (left)) or Cos1 cells (right), which are phenotypically null for Tie-2 expression. Cells were infected with recombinant adenovirus encoding EGFP (Ad-EGFP lanes) or Tie 2 (Ad-Tek lane; positive control.) Cells infected with Ad-EGFP were stimulated with unclustered or clustered Vasculotide, neither of which were able to stimulate phosphorylation of AKT or MAPK above basal unstimulated levels.

Cells infected with recombinant adenovirus encoding EGFP or Tie 2 were either left unstimulated or stimulated with Vasculotide, clustered Vasculotide or avidin for 16 hours, after which MTS reagent was applied to all samples for 4 hours. Absorbance at 492 was measured using a multiwell plate reader (Power Wave X340, Biotek Instruments Inc). To broadly examine the potential that clustered Vasculotide was activating Tie 2-independent downstream signalling pathways, the activation of MAPK and AKT in the EGFP infected cells was examined. The results are shown in FIG. 1F. Neither Vasculotide nor clustered Vasculotide significantly induced phosphorylation of MAPK or AKT in the EGFP infected cells above that noted in the non-stimulated samples. As expected, overexpression of Tie 2 in either of the cell types resulted in its constitutive activation (see pY992 Tie 2) as well as activation of MAPK and AKT. This fact precluded us from stimulating these cells any further with Vasculotide or clustered Vasculotide. Because MAPK and AKT are highly activated downstream of a host of cell surface receptors we reason that these results are highly suggestive of a Tie 2 specific and dependent role for clustered Vasculotide in these events.

Example 4

Effects of Vasculotide on Endothelial Cell Apoptosis and Migration

Figure 2A:
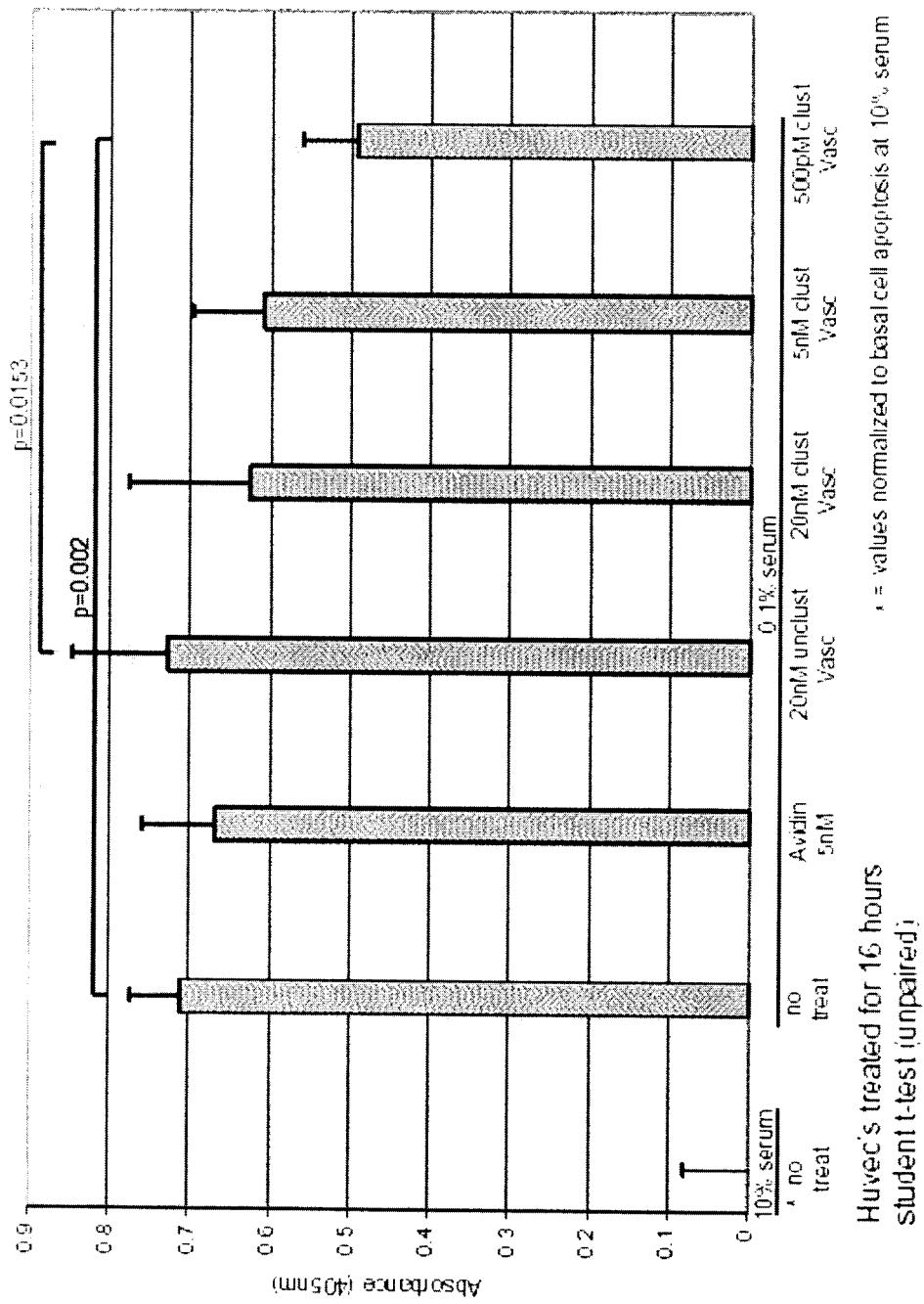
FIG. 2A is a bar graph of results from a cell death ELISA experiment, showing that clustered Vasculotide reduces serum withdrawal-induced cell death of HUVEC cells.

Ang 1, and to a lesser degree Ang 2, have been shown to protect endothelial cells (ECs) from various different apoptosis-inducing conditions including serum withdrawal (Kwak, H et al. (1999) *FEBS Lett.* 2-3:249-253; Harfouche, R. and Hussain, R. (2006) *Am. J. Physiol. Heart Circ. Physiol.* 291:H1635-1645). Based on the fact that clustered Vasculotide strongly activates the anti apoptotic protein AKT (see Example 3), the ability of Vasculotide to protect ECs from serum withdrawal-induced death was examined. To do so, HUVEC were maintained in F12 media plus 0.1% FBS for 16 hours in the presence of various concentrations of unclustered or clustered Vasculotide, followed by analysis of cell apoptosis via cell death ELISA. Analysis of apoptosis was performed using Cell Death ELISA Plus (Roche) according to manufacturers' specifications. The results are shown in FIG. 2A, in which values were normalized to basal levels of cell death for HUVECs maintained in full 10% FBS, growth factor supplemented F12 media. The results shown represent the mean of three replicates plus or minus 1 SD. Student's T-test was used for statistical analysis with P value indicated. The results revealed a statistically significant decrease in apoptosis when the ECs were treated with clustered Vasculotide at 500 pM (p=0.002) compared to non-treated cells. Non-clustered Vasculotide and avidin alone had no effect on survival, further illustrating that Vasculotide is only active when preclustered with avidin.

EC migration is an event deemed critical to revascularization upon injury. Migration must take place in a coordinated fashion, with the ECs responding to chemotactic signals from the stroma and in turn secreting proteases necessary to clear a path for their directional migration. Previous studies underline a role for Ang 1 in promoting EC migration and release of the matrix degrading enzyme MMP 2 (Kim, I. et al. (2000) *Circ. Res.* 9:952-959; Witzenbichler, B. et al. (1998) *J. Biol. Chem.* 29:18514-18521). To test if Vasculotide, like Ang 1, was capable of promoting these processes, the effect of Vasculotide on EC migration was tested using a modified Boyden chamber assay. HUVEC were seeded at a density of $8.4 \times 10^4$ cells in 500 µl of F12 growth media plus 0.1% FBS in the upper chamber of an 8 µm pore size modified Boyden chamber (Falcon). 500 µl of F12 media plus 0.1% FBS plus various growth factors (Ang 1 (R& D Systems), unclustered or clustered Vasculotide, VEGF (R&D Systems) or clustered Vasculotide in combination with VEGF) or controls were placed in the bottom chamber. Cells were allowed to migrate for 4 hours in a 37° C., 5% $CO_2$ incubator. Nonmigrating cells were scraped off, and filters were fixed in 100% methanol for 5 minutes, stained with Harris' Hematoxylin (BDH) for 10 minutes and washed twice with tap water for 3 minutes each. Filters were then mounted using Aquapolymount mounting medium. Cells that had migrated more than 50% of the way through the pore were scored as positive for migration.

Figure 2B:
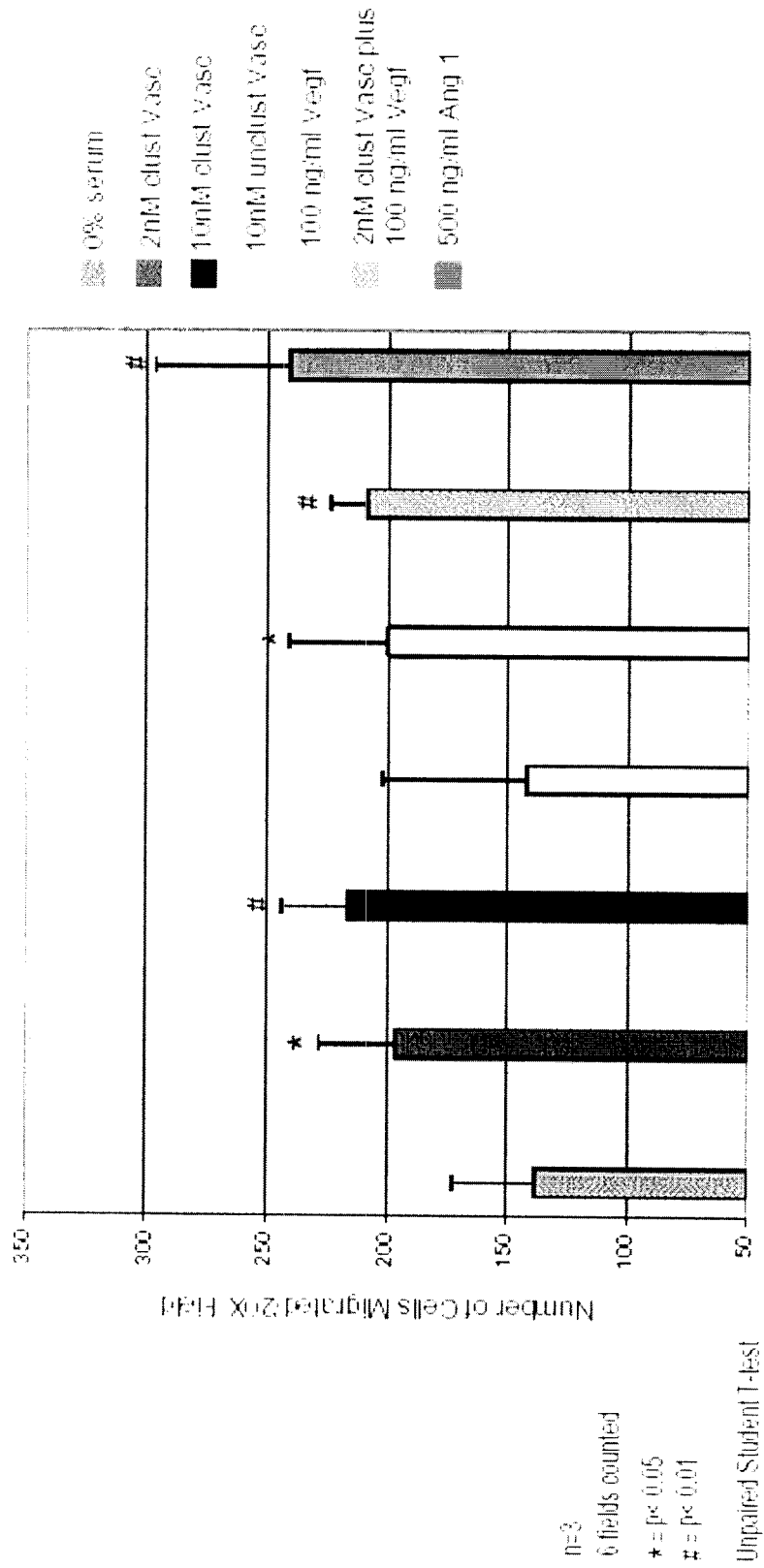
FIG. 2B is a bar graph of results from a modified Boyden chamber migration assay, showing that clustered Vaculotide promotes chemotactic cell migration that is statistically indistinguishable from migration induced by VEGF (100 ng/ml) or Ang 1 (500 ng/ml).

The results are shown in FIG. 2B. Student's t test was used to test the statistical significance with a 95% confidence interval. Stimulations were performed in triplicate and migrating cells in 6 microscopic fields per replicate were counted. Error bars shown in FIG. 2B represent mean+/−SD. The results showed that clustered Vasculotide, at both doses examined (2 nM and 10 nM), promoted significant increases in chemotactic cell migration when compared to no treatment. Noted migration was not significantly different than that seen in samples treated with VEGF or Ang 1. Non clustered Vasculotide did not promote migration above that seen in the untreated sample and the combination of VEGF and clustered Vasculotide did not offer any additional effect beyond that observed for either VEGF or clustered Vasculotide alone.

Figure 2C:
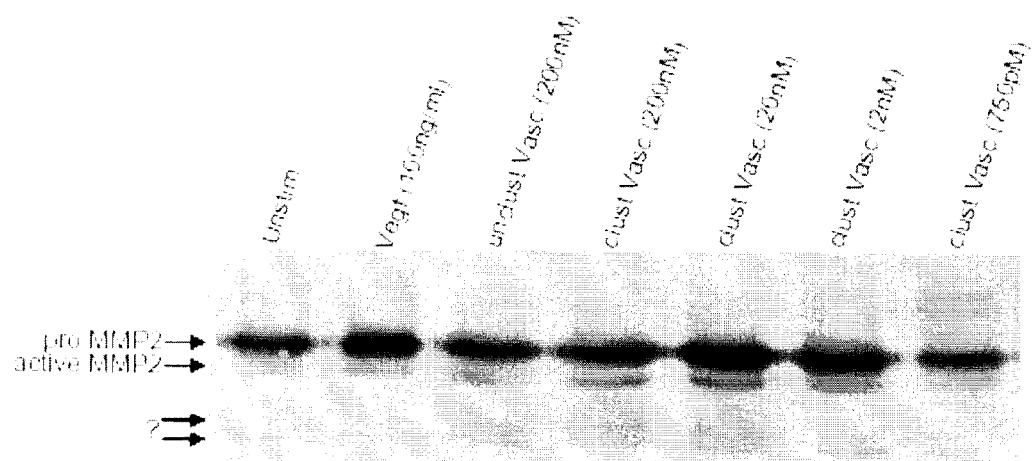
FIG. 2C is a gelatin zymographic analysis of conditioned media from HUVEC cells stimulated with VEGF, unclustered Vasculotide or clustered Vasculotide, indicating a role for clustered Vasculotide in promoting release of MMP2.

In vivo, ECs can not migrate until they secrete enzymes necessary to break down components of the extra cellular matrix. Gelatin zymography was employed to determine if clustered Vasculotide promoted secretion of MMP2. To perform the zymography, HUVEC were cultured in F12 media plus 0.1% FBS and stimulated for 16 h with VEGF, unclustered Vasculotide or clustered Vasculotide at various concentrations. Conditioned media was centrifuged to remove cellular debris and prepared for gel electrophoresis using non-reducing conditions. Gels were washed twice for 30 minutes in 2.5% Triton X-100 to remove sodium dodecyl sulfate and were then incubated in substrate buffer (50 mmol/L Tris-HCl, pH 8.8, 5 mmol/L $CaCl_2$) for 16 hours at 37° C. Gels were then stained with 0.5% Coomassie blue in 30% methanol/10% acetic acid for 2 hours at room temperature and destained in 50% methanol/10% acetic acid. The presence of metalloproteinases was indicated by unstained proteolytic zones in the gel. The results are shown in FIG. 2C. Analysis of the conditioned media revealed that clustered Vasculotide dose-dependently degraded gelatin at a molecular weight that was consistent with pro and active forms of MMP2. Taken together with the results of the migration analysis, this data indicates that application of clustered Vasculotide can offer distinct advantages in vivo to migrating endothelial cells.

Example 5

Promotion of Angiogenesis by Vasculotide in a Matrigel Assay

To further examine the in vivo angiogenic potential of Vasculotide, a Matrigel assay was performed. More specifically, growth factor reduced Matrigel (BD Biosciences) was impregnated with either clustered Vasculotide or one of several different control factors. These Matrigel samples were injected subcutaneously into the flank region of 3 month old CD1 mice. 14 days post implantation and immediately prior to sacrifice, FITC lectin (100 µg) was injected IV and allowed to circulate for 10 minutes, to facilitate vessel identification and quantification. Plugs were surgically resected and fixed in 4% paraformaldehyde (PFA) for 16 h. Images of vascular topology were taken using a Zeiss dissecting microscope at 4× magnification. Upon fixing, all plugs were whole mount stained with anti-Sma1-Cy3. Plugs were analyzed on a Zeiss Axiovert 100 M confocal microscope (Carl Zeiss) for three dimensional image reconstruction and photos were processed using LSM Image Browser and Adobe Photoshop 7.0. Morphometric quantification of vessel characteristics was performed by skeletonizing confocal image projections with Image Processing Tool Kit 5.0 (IPTK 5.0). Student's t test was used to test the statistical significance with a 95% confidence interval. All experiments were performed with three replicates each, with at least 5 random image stacks.

Upon surgical removal of the plugs, a distinct and robust angiogenic response was seen in the membranous capsule that surrounded the plugs impregnated with clustered Vasculotide, VEGF or clustered Vasculotide plus VEGF. In the case of the clustered Vasculotide samples, clear, large, well arborized vessels were present on the surface. These vessels were well branched and contained a continuum of small and large arterioles and venules. Consistent with literature accounts (Connolly, D. et al. (1989) *J. Clin. Invest.* 5:1470-1478), vessel growth promoted by the addition of VEGF alone was apparent, although the nature of these vessels was highly tortuous. Vessels located in the proximal tissue surrounding these plugs also looked enlarged and inflamed upon examination. Application of clustered Vasculotide in combination with VEGF did not seem to increase the overall microvascular density but rather contributed to decreases in the level of the tortuosity seen with VEGF alone.

Figure 3B:
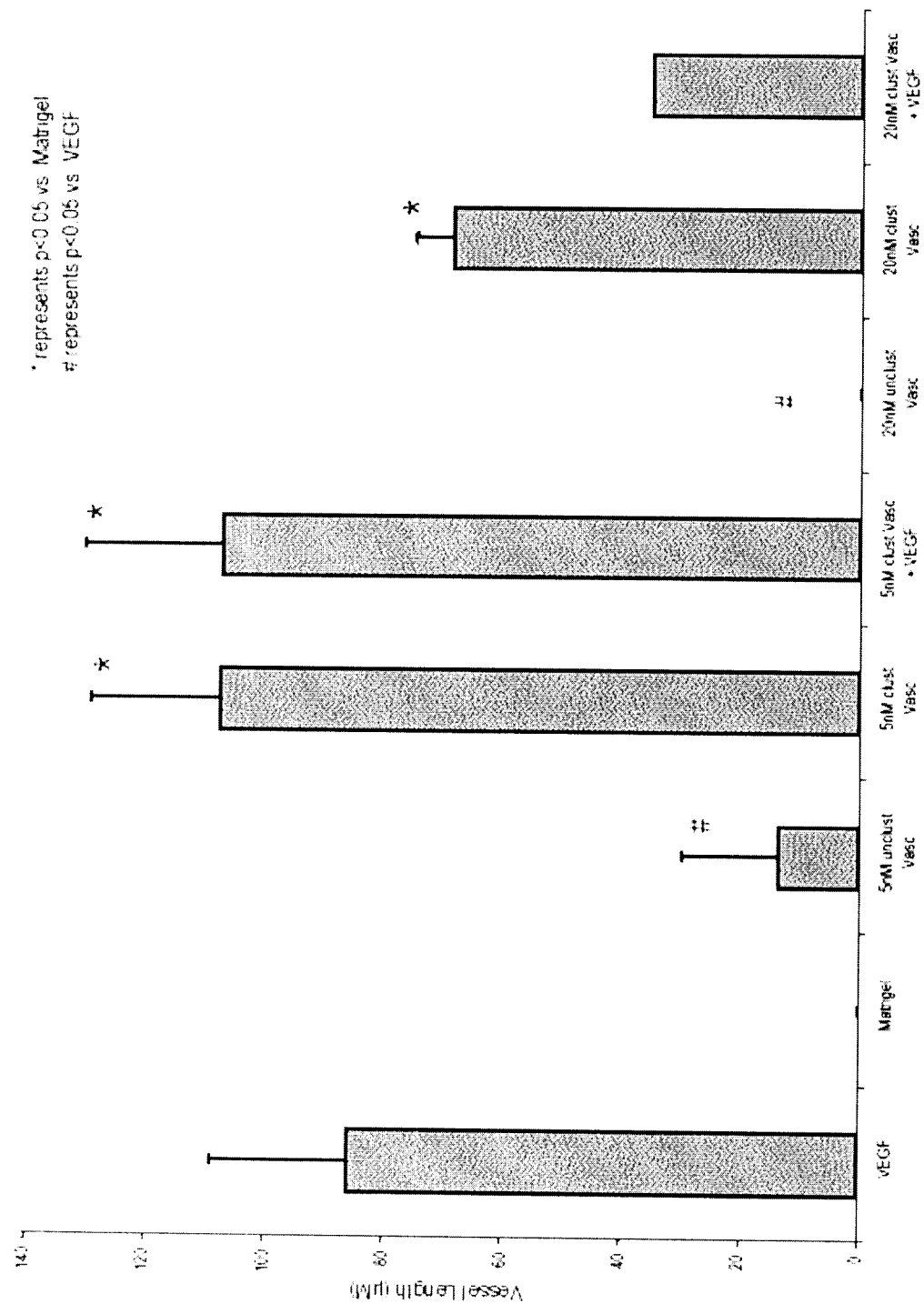
FIG. 3B is a bar graph of the results of a Matrigel assay, quantifying the vessel length in each treatment group, showing that clustered Vasculotide, alone or in combination with VEGF, increases vessel length.
Figure 3C:
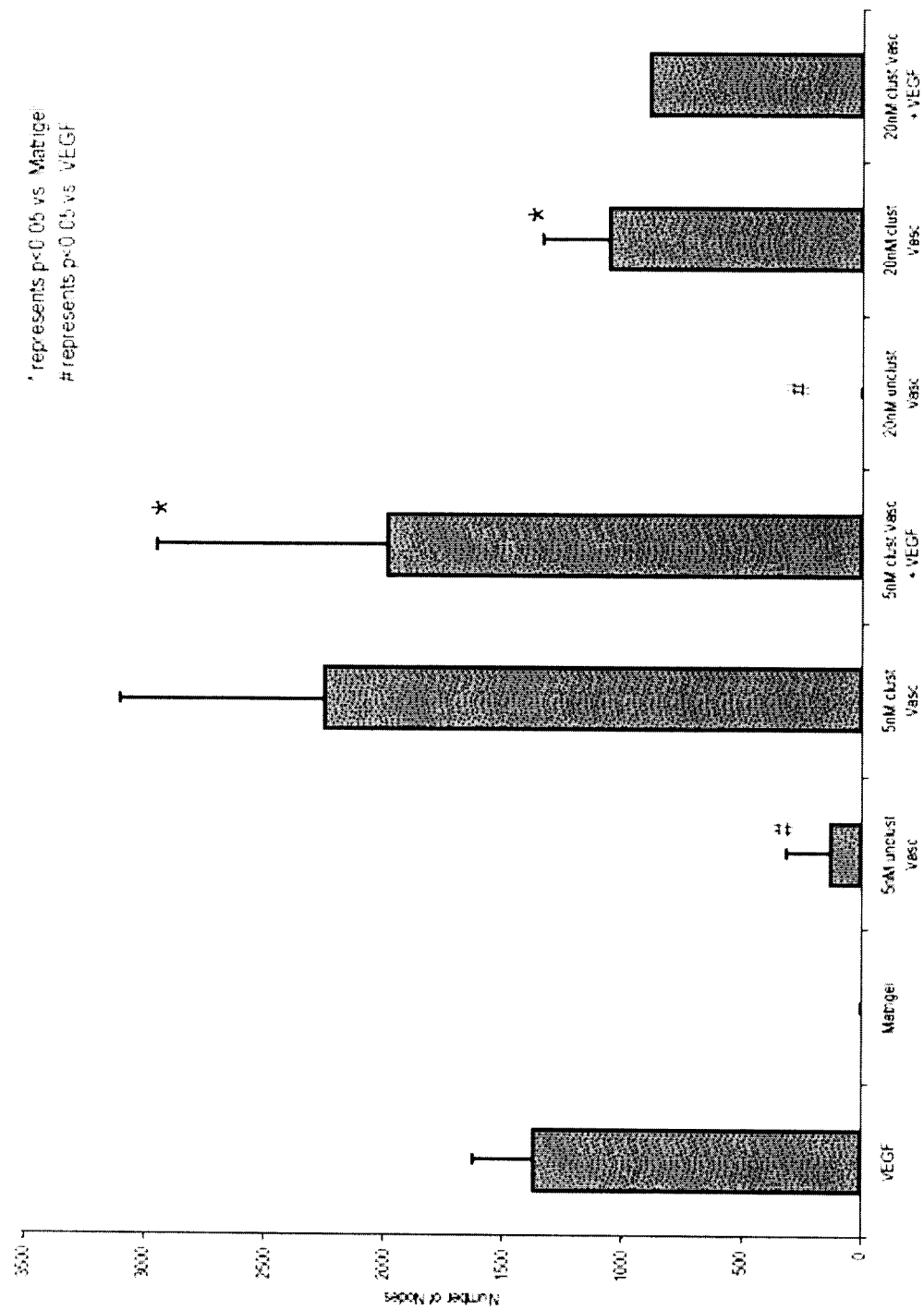
FIG. 3C is a bar graph of the results of a Matrigel assay, quantifying the number of nodes in each treatment group, showing that clustered Vasculotide, alone or in combination with VEGF, increases node number.

To more fully address and assign quantitative vessel parameters to the different treatment groups, the plugs were fixed and interrogated with laser confocal microscopy analysis combined with post processing image analysis (Image Processing Tool Kit 5.0, Reindeer Graphics, N.C.). Vessel parameters, including length, number and branch points (nodes) were quantified on at least six representative fields. Statistical analysis was performed by way of unpaired Student's t test. Bar graphs of the number of vessels, vessel length and number of nodes, for each treatment group, are shown in FIGS. 3A, 3B and 3C, respectively. It is noted that poor perfusion of FITC-lecithin into mice harboring 20 nM clustered Vasculotide plus VEGF plugs prevented statistical analysis, therefore bars are the mean of two separate fields. All other bars shown represent mean+/−SD. The results show that no significant vessel growth was noted in plugs containing Matrigel or Matrigel impregnated with non clustered Vasculotide. Plugs containing VEGF, clustered Vasculotide or clustered Vasculotide plus VEGF displayed robust induction of angiogenesis. Statistically, VEGF, Vasculotide or combinations thereof did not differ in total vessel number, length or branch points. As was noted in the membranous capsule, samples that contained Vasculotide displayed more organized branching patterns and less tortuosity than the plugs containing VEGF alone (however these were parameters that could not specifically be quantified by assignment of a numerical value).

Ang 1 has been reported to potentiate the recruitment of myogenic support cells (Suri, C. et al. (1996) *Cell* 87:1171-1180) and inhibit VEGF induced vascular permeability through mechanisms that are not well understood (Thurston, G. et al. (2000) *Nat. Med.* 6:460-463). To determine if Vasculotide, like Ang 1, was capable of initiating pericyte recruitment, whole mount immunofluorescence was performed against smooth muscle actin 1 (Sma1). Matrigel plug analysis of VEGF driven angiogenesis revealed a relative absence of Sma1 positive staining cells. Samples containing clustered Vasculotide alone or in combination with VEGF displayed a significant increase in overall Sma 1 staining. Sma 1 staining was tightly associated with the exterior of the vessels and was enriched on larger vessels. Taken together these results demonstrate potent in vivo angiogenic effects of clustered Vasculotide and indicate that, when combined with VEGF, clustered Vasculotide is capable of counteracting VEGF induced permeability and aberrant vessel formation.

Example 6

Wound Healing by Topically Administered Vasculotide

Chronic wounds, such as neuropathic or neuroischemic foot ulcers, are prevalent in diabetic patients. These wounds may arise from the patient's inability to sense injury (neuropathic) or due to microvascular defects (neuroischemic). Animal models of type II diabetes exist and closely recapitulate wound healing defects seen in human diabetics. Here, B6.Cg-m(+/+)Lepr(db)/J (db/db) mice, a strain of diabetic mice that presents with impaired wound healing, were used to test if clustered Vasculotide could improve wound closure times.

Pathogen free, nine week old B6.Cg-m(+/+)Lepr(db)/J (db/db) mice were purchased from Jackson Laboratories. Circular, full excisional, 6 mm diameter wounds were made, according to animal committee approval guidelines, equal distant apart on the dorsal side of the mice. Various factors were suspended in sterile Intrasite Topical Gel (Smith and Nephew) at noted concentrations. Treatments were as follows: Vehicle n=8, bFGF (10 µg/ml) n=8, clustered Vasculotide (20 nM) n=4, clustered Vasculotide (5 nM) n=4. Preparations were applied at day 0 (time of wounding), day 2, 4 and 6. Standardized images were taken on days 0, 2, 4, 6 and 7 using a Canon EOS digital Rebel camera. Image J (NIH) was used to manually outline wound perimeter from which total pixel counts (wound area) were determined. Mice were sacrificed on day 7 and full wound beds including margin were excised and fixed in 4% PFA. Wounds were cut in half at the widest point and each half was prepared for either paraffin or frozen sections. Wax sections were processed according to standard protocols for H&E and Masson's Trichrome stain. Images were captured using a Leica DMLS compound light microscope and Pixel Link camera at 5× and 20×. Student's t test was used to test the statistical significance.

Figure 4A:
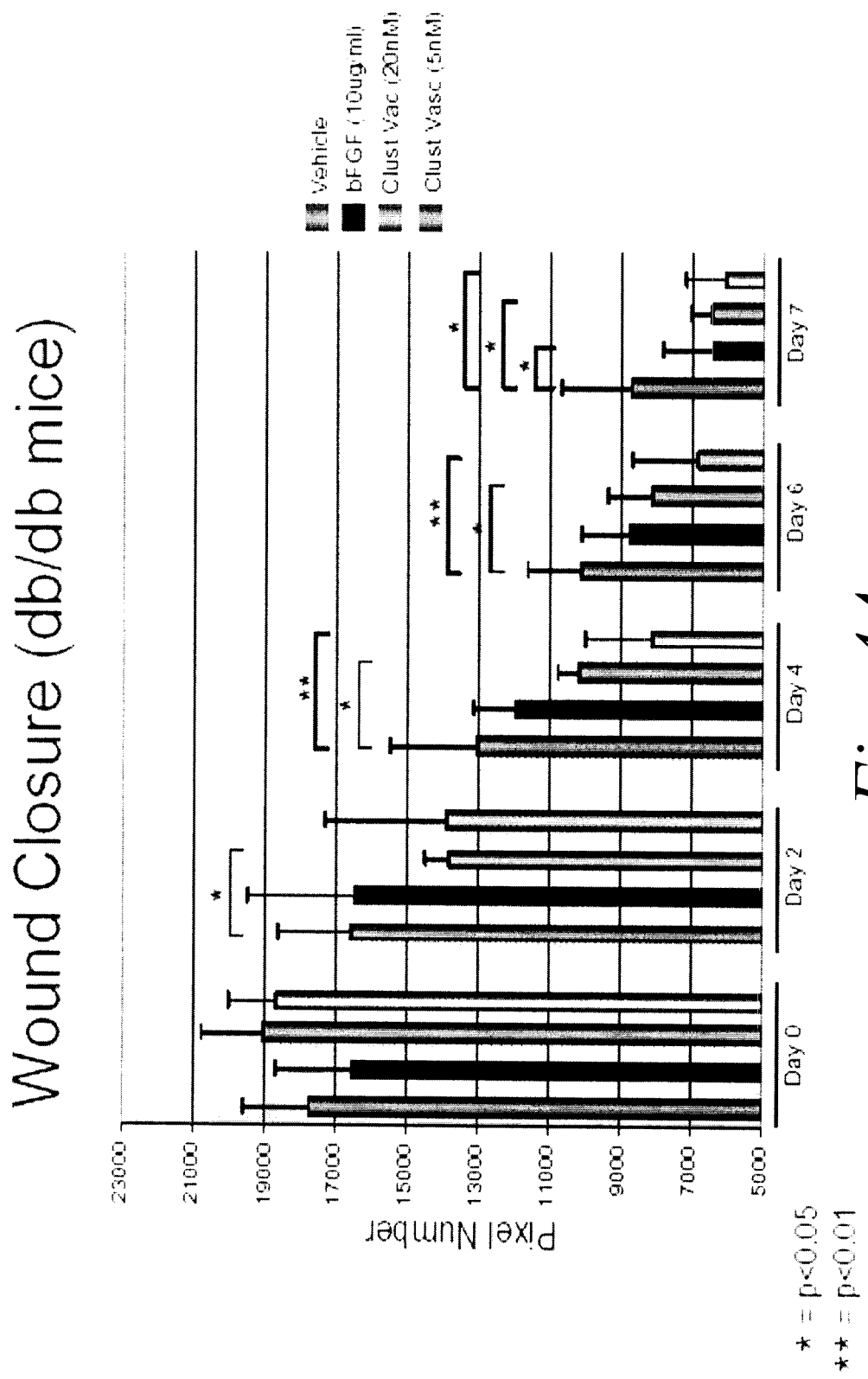
FIG. 4A is a bar graph of the results of a wound closure assay, quantifying total pixel counts of digital tracings of wound margins over time, showing that treatment with clustered Vasculotide led to decreases in wound margin as early as day 2 of treatment.

The wound closure data is summarized in the bar graph of FIG. 4A, in which the data is presented as pixel counts of digital tracings of the wound margins over time. All bars shown represent mean+/−S.D. Significant decreases in wound margin in the clustered Vasculotide samples (20 nM, p=0.05, n=4) were noted as early as day 2. Coincident with improved wound closure was a change in the appearance of the wounds treated with clustered Vasculotide. These wounds presented with a lighter more mucoid looking scab. Margin closure in the clustered Vasculotide treated wounds continued at an accelerated pace for the duration of the assay. As was the case in vitro, clustered Vasculotide applied at lower concentration seemed to offer more benefit. Although this may seem unusual, similar results were also noted with topical application of Regranex, a topical preparation of modified PDGF (Mustoe, T. et al. (1994) *Arch. Surg.* 129:213-219). Moreover, these results further highlight the need to optimize the Vasculotide:Tie 2 ratio to facilitate appropriate clustering of the receptor. Although Vasculotide provided the fastest healing at early time points, by day 7 of the treatment wound closure promoted by bFGF at 10 µg/ml was statistically indistinguishable from clustered Vasculotide at 20 nM or 5 nM.

Figure 4B:
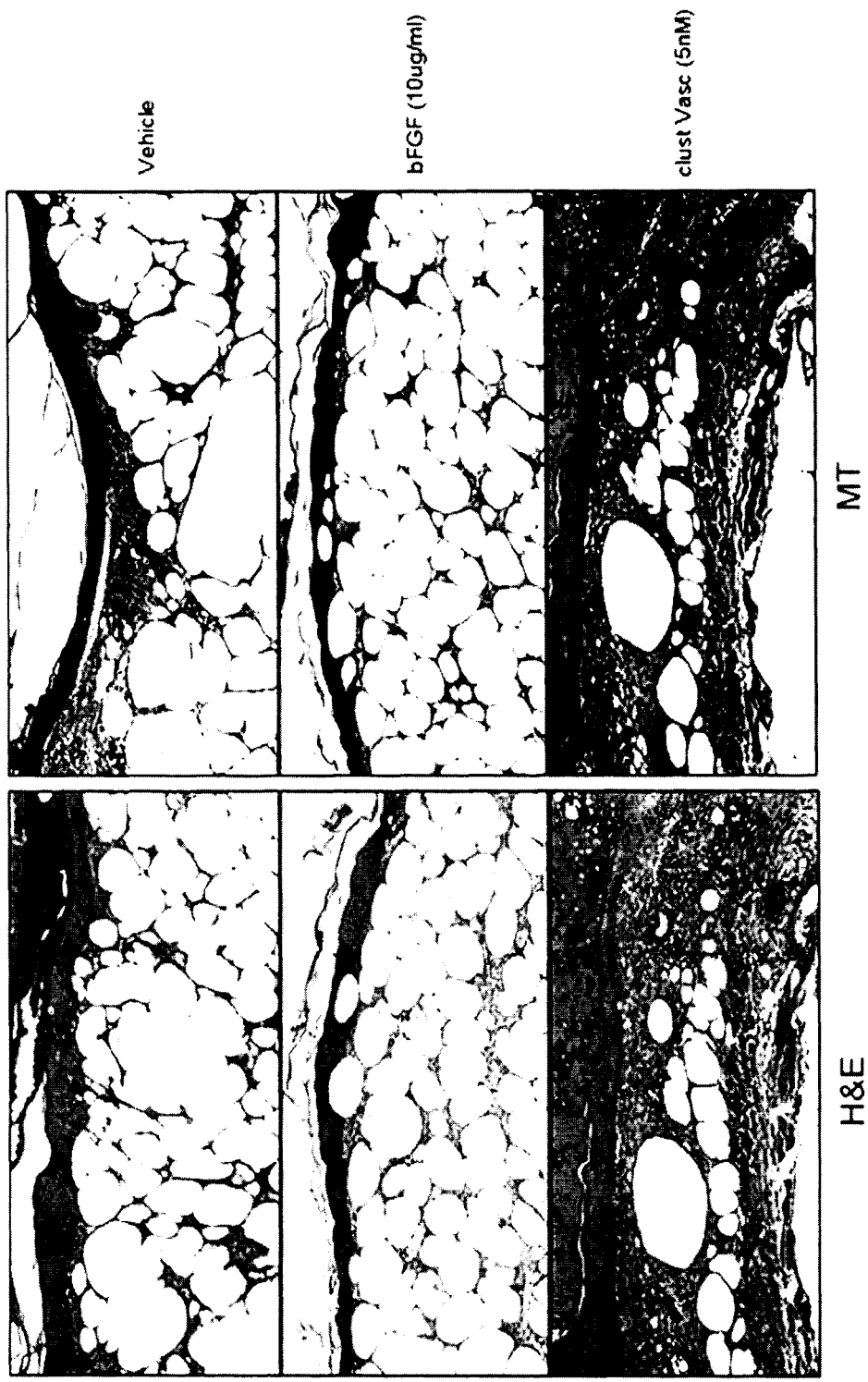
FIG. 4B is a representative photomicrograph of hematoxylin eosin (H&E) and Masson's trichome (MT) stained skin sections from wounds treated with PBS, bFGF (10 µg/ml) or clustered Vasculotide (5 nM).

Paraffin embedded cross sections of all wounds stained with hematoxylin and eosin (H & E) and Masson's trichrome were examined by a pathologist for independent blind analysis. A representative photomicrograph of the hematoxylin eosin (H&E) and Masson's trichrome (MT) stained skin sections from wounds treated with PBS, bFGF (10 µg/ml) or clustered Vasculotide (5 nM) is shown in FIG. 4B. The H&E and MT staining showed dramatic increases in granulation tissue production in all Vasculotide treated wounds. Additionally, the MT staining revealed marked collagen deposition in the Vasculatide treated samples.

For histological scoring, sections were fixed in 4% paraformaldehyde, embedded in paraffin and sectioned and stained with H & E and Masson's trichrome. Sections were evaluated by a pathologist for re-epithelialization, granulation tissue formation, and inflammation, with criteria used for scoring skin as follows:

Re-Epithelialization:
0—none
1—minimal (0-20% regrowth from wound margins)
2—mild (25% to 50% regrowth)
3—moderate (>50% regrowth, up to 100% but not >2 cells thick along length)
4—complete regrowth (epithelium>1 cell thick along length, keratinized)

Granulation Tissue (GT) and Neovascularization:
0—none
1—minimal (1-3 small, isolated islands of GT at margins of defect)
2—mild (multifocal, patchy islands of GT underlying tissue defect, <10 new blood vessels)
3—moderate (locally extensive bands of GT underlying length of defect)
4—marked (dense bands of GT at margins and underlying length of defect with collagen fibrils and numerous blood vessels)

Inflammation (within Defect):
0—none
1—minimal (a few scattered neutrophils at margins of defect)
2—mild (multifocal aggregates of up to 5 neutrophils underlying defect)
3—moderate (multifocal aggregates of up to 10 neutrophils and occasional macrophages, minimal to mild edema)
4—marked (locally extensive, dense neutrophilic infiltrates with lesser numbers of macrophages, mild-moderate edema)

Figure 4C:
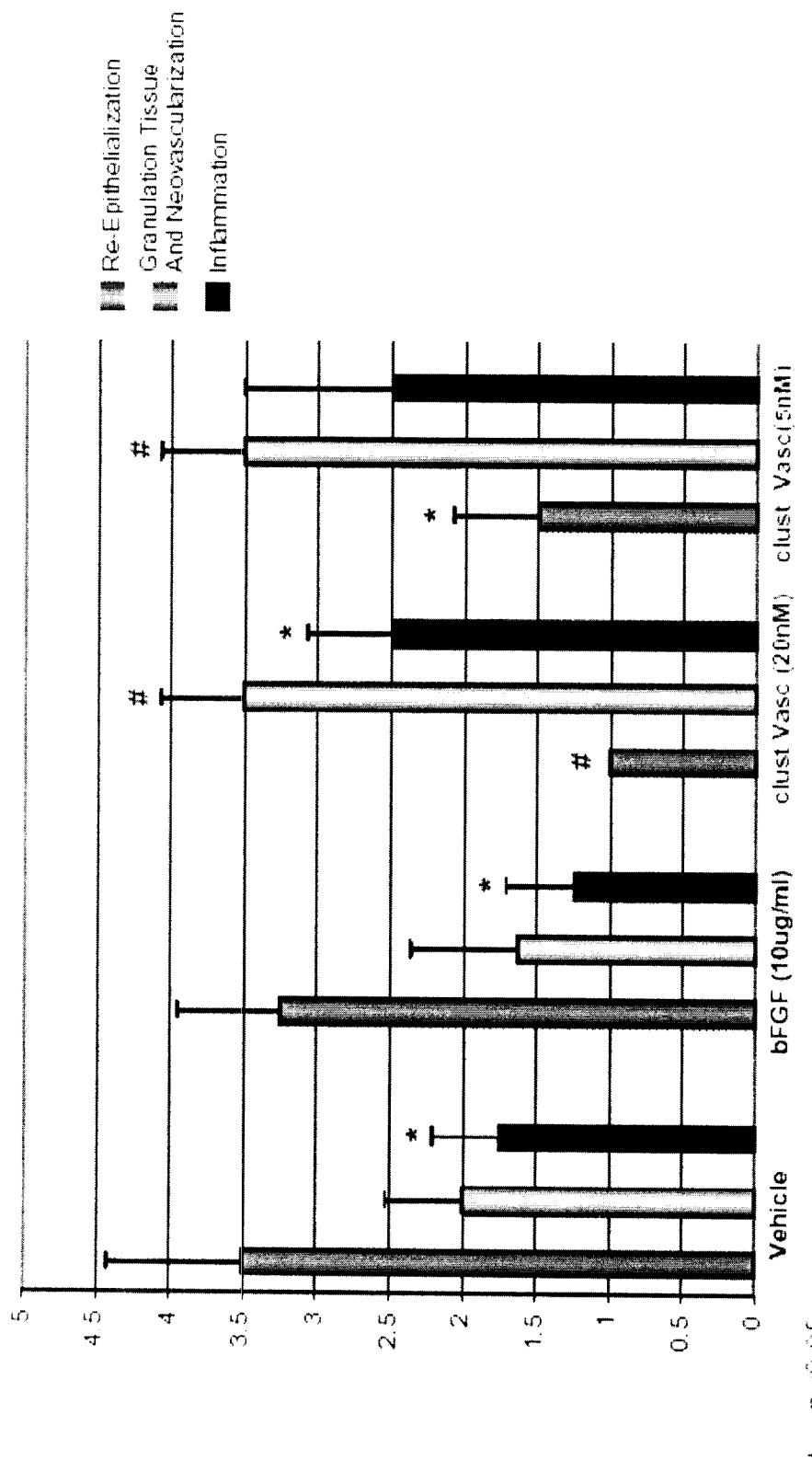
FIG. 4C is a bar graph of the results of histological scoring of a wound closure assay, quantifying re-epithelialization, granulation tissue and neovascularization and inflammation using a 0-4 scale, showing that treatment with clustered Vasculotide resulted in delayed re-epithelialization but promoted profound increases in regranulation and neovascularization.

The results of the histological scoring are illustrated in FIG. 4C. Differences between vehicle and bFGF, although apparent in wound closure times, existed only at the level of inflammation (p=0.0486). Application of clustered Vaculotide resulted in delayed re-epithelialization (20 nM, p=0.0004 and 5 nM, p=0.029) but promoted profound increases in regranulation and neovascularization (20 nM and 5 nM p=0.0006). Inflammation noted in the clustered Vasculotide samples was only slightly increased at 20 nM (p=0.034) and was not significantly different from vehicle at the 5 nM dose (p=0.0979).

Immunohistochemical analysis of the wounds with antibodies directed against PECAM1, 1CAM 1, Pan EC, podoplannin, and smooth muscle actin demonstrated clear differences between clustered Vasculotide-treated and untreated samples. First, it is noted that histopathological examination of the stained tissues from 5 nM and 20 nM clustered Vasculotide treatments revealed no statistically significant differences in the results for the doses of Vasculotide used. At both Vasculotide doses, increases in total endothelial cells (PECAM staining), activation of endothelial cells (ICAM1 staining) and fibroblast activation (Sma 1 staining) were observed in all Vasculotide treated wounds. Furthermore, wounds treated with clustered Vasculotide displayed dramatic increases in the number of PECAM1- and Pan EC-positive vessels within the granulation tissue. Importantly many of the new vessels in the granulation tissue were accompanied by SMA-positive support cells. Furthermore, these vessels were also positive for ICAM 1, a marker of activated endothelial cells, demonstrating an active wound healing process was occurring. The increase in vessel density was surprisingly not accompanied by an increase in lymphangiogenesis, as detailed by similar numbers of podoplannin-positive vessels. Overall collagen deposition, as assessed by Masson's Trichrome staining, was dramatically increased at both of the clustered Vasculotide concentrations compared to the vehicle and bFGF samples. Collagen deposition, primarily mediated by activated fibroblasts, plays a necessary role in contracting the wound margins, offers tensile strength, provides a scaffold for neovascularisation and facilitates cellular signalling to migrating cells via integrin engagement. Based on pathological and immunohistochemical analysis we conclude that the improved wound closure times noted in the clustered Vasculotide samples are a likely consequence of strong contraction effects brought about by increases in collagen deposition and neovascularisation.

Example 7

Systemic Administration of Vasculotide

In this example, the effect of systemically administered Vasculotide on circulating endothelial cells was examined. Three month old CD1 mice were injected intravenously with either PBS (vehicle) or 50 µg of clustered Vasculotide. Twenty four hours post injection, peripheral blood was collected on heparin via cardiac puncture and nonhematopoietic circulating endothelial cells (CECs) were sorted using a four channel FACS approach. CECs were defined as $CD13^+$/$VEGFR-2^+$/$CD45^-$, Viable (propidium iodide). Cell numbers reported are number of viable cells/µl of peripheral blood. Total white blood cell count was also determined using a hemocytometer.

The results demonstrated that systemic delivery of Vasculotide was well tolerated and resulted in a decrease in the number of circulating endothelial cells. This has also been described for Ang-1 delivered by adenoviral infection, suggesting that Vasculotide has similar properties in the stem cell niche as Ang-1.

Example 8

Multimeric Tie 2 Agonist Comprising a GA3 Peptide

In this example, an alternative form of the Vasculotide molecule was prepared in which a GA3 peptide was used instead of a T7 peptide. The amino acid sequence of the GA3 peptide was as follows: Trp-Thr-Ile-Ile-Gln-Arg-Arg-Glu-Asp-Gly-Ser-Val-Asp-Phe-Gln-Arg-Thr-Trp-Lys-Glu-Tyr-Lys (SEQ ID NO: 3). To facilitate further modification of the peptide, it was synthesized, as described in Example 1, with an additional amino terminal cysteine residue such that the amino acid sequence of the peptide used in the multimeric form was as follows: Cys-Trp-Thr-Ile-Ile-Gln-Arg-Arg-Glu-Asp-Gly-Ser-Val-Asp-Phe-Gln-Arg-Thr-Trp-Lys-Glu-Tyr-Lys (SEQ ID NO: 4). The cysteine-containing peptide was conjugated to biotin using EZ-link-PEO-maleimide-biotin (Pierce's catalog number 21901) as described in Example 1. Post synthesis clustering of this biotinylated peptide-PEG with avidin in a 4:1 ratio gave rise to an obligate tetrameric compound.

Figure 5A:
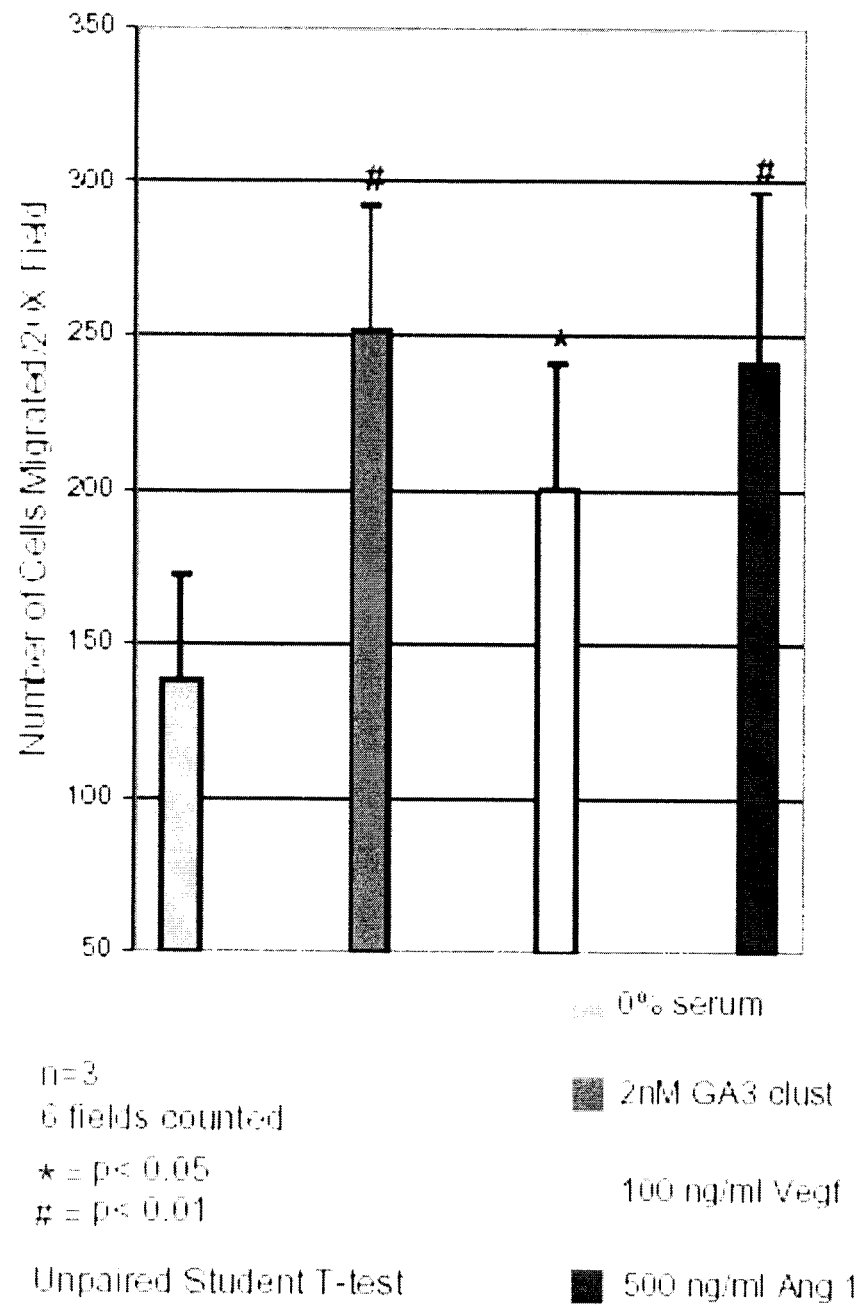
FIG. 5A is a bar graph of the results from a modified Boyden chamber migration assay, showing that a multimeric GA3 peptide-containing compound promotes chemotactic cell migration.

The tetrameric GA3-containing compound was tested in the endothelial cell migration assay as described in detail in Example 4. The results are shown in FIG. 5A, which demonstrate that the tetrameric GA3-containing compound was effective in promoting endothelial cell migration.

Figure 5B:
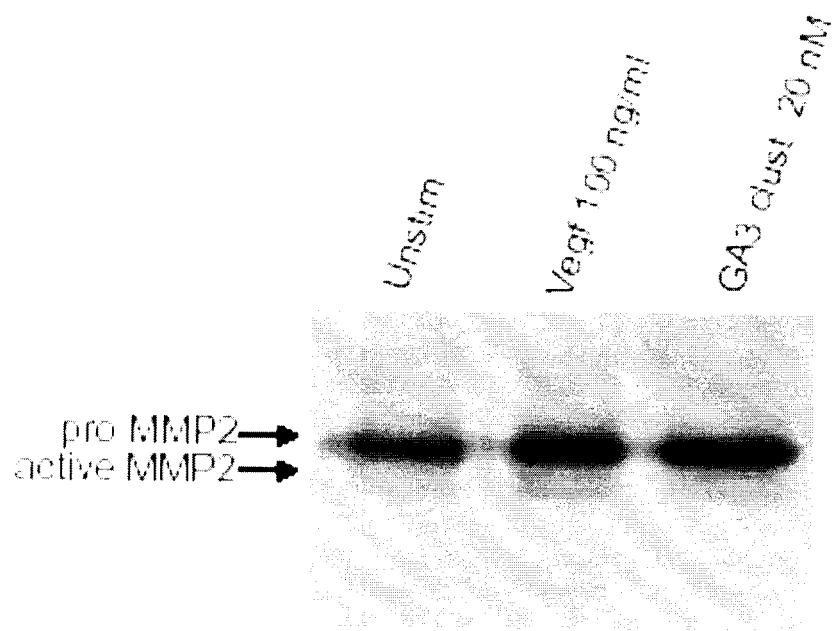
FIG. 5B is a gelatin zymographic analysis of conditioned media from HUVEC cells stimulated with a multimeric GA3 peptide-containing compound, demonstrating that the compound can promote release of MMP2.

The tetrameric GA3-containing compound also was tested in the zymography assay as described in detail in Example 4. The results are shown in FIG. 5B, which demonstrate that the tetrameric GA3-containing compound was effective in promoting MMP2 release.

These results demonstrate the agonist activity of a second multimeric Tie 2 binding peptide containing compound, wherein the compound contains a GA3 peptide rather than a T7 peptide.

Example 9

Preparation of PEG-Linked Multimeric Tie 2 Agonists

In this example, multimeric Tie 2 agonists were prepared using polyethylene glycol (PEG) linkers to covalently join the peptide components of the agonists. Three different PEG-linked Tie 2 agonists were prepared: (i) an agonist in which two T7 peptides were joined using a 10,000 Dalton MW PEG linker; (ii) an agonist in which two T7 peptides were joined using a 20,000 Dalton MW PEG linker; and (iii) an agonist in which four T7 peptides were joined using a 20,000 Dalton MW tetrameric PEG linker. To prepare these molecules, activated branched arm PEGs were purchased from NOF America. PEGs used in this example were Sunbright DE-100MA (PEG dimaleimide MW 10,000 Da, terminal activity 79%), Sunbright DE-200MA (PEG dimaleimide MW 20,000 Da, terminal activity 85.1%) and Sunbright PTE-200MA (PEG tetramaleimide MW 20,000 Da, terminal activity 94%). T7 peptide was reacted with activated PEGs as follows: In the case of the two dimaleimide PEGs exactly two molar equivalents of T7 peptide and 1 molar equivalent of dimaleimide PEG were dissolved in phosphate buffered saline (PBS), pH 7.2. In the case of tetramaleimide PEG exactly four molar equivalents of T7 peptide and 1 molar equivalent of tetramaleimide PEG were dissolved in PBS, pH 7.2. Reactions were allowed to proceed at 21° C. for 16 hours The structures of the resultant multimeric Tie 2 agonists are illustrated schematically in FIG. 6. These PEG-linked, T7 peptide-containing multimeric Tie 2 agonists are referred to herein as PEG-T7 Vasculotide.

Example 10

Characterization of the Tie 2 Activation by PEG-Vasculotide

In this example, the ability of the PEG-T7 Vasculotide compounds, prepared as described in Example 9, to activate the Tie 2 receptor was examined in an in vitro Tie 2 activation assay. PEG-T7 Vasculotide compounds were used in endothelial cell stimulations as follows. Purified bovine vascular endothelial cells (bVEC) were grown on 6-well plates (Nunc) in Dulbecco's modified Eagle's medium (DMEM) supplemented with 10% (FBS), 1× penicillin, 1× streptomycin, and 200 mM L-glutamine (all Gibco BRL) in a 5% $CO_2$ incubator at 37° C. The bVECs were stimulated with either PBS, tetrameric PEG-T7 Vasculotide MW 20,000 Daltons (PTE200-T7; 5 μg/ml) or dimeric PEG-T7 Vasculotide MW 10,000 Daltons (DE100-T7; 250 ng/ml or 500 ng/ml) for 10 minutes. Cell lysates were prepared in RIPA lysis buffer (50 mM Tris pH 7.5, 150 mM NaCl, 1% Igepal, 0.5% sodium deoxycholate, 0.1% sodium dodecyl sulphate, 1× aprotinin, 1× leupeptin and 1×PMSF). Equal quantities of cellular protein were electrophoretically resolved and transferred to PVDF membrane for immunoblot analysis. Immunoblot analysis was performed according to standard practices, using monoclonal anti-Tie 2 antibody (Pharminogen) and polyclonal anti-pY992 Tie 2 antibody (Cell Signaling Technology), and employing horse radish peroxidise detection methods.

Figure 7:
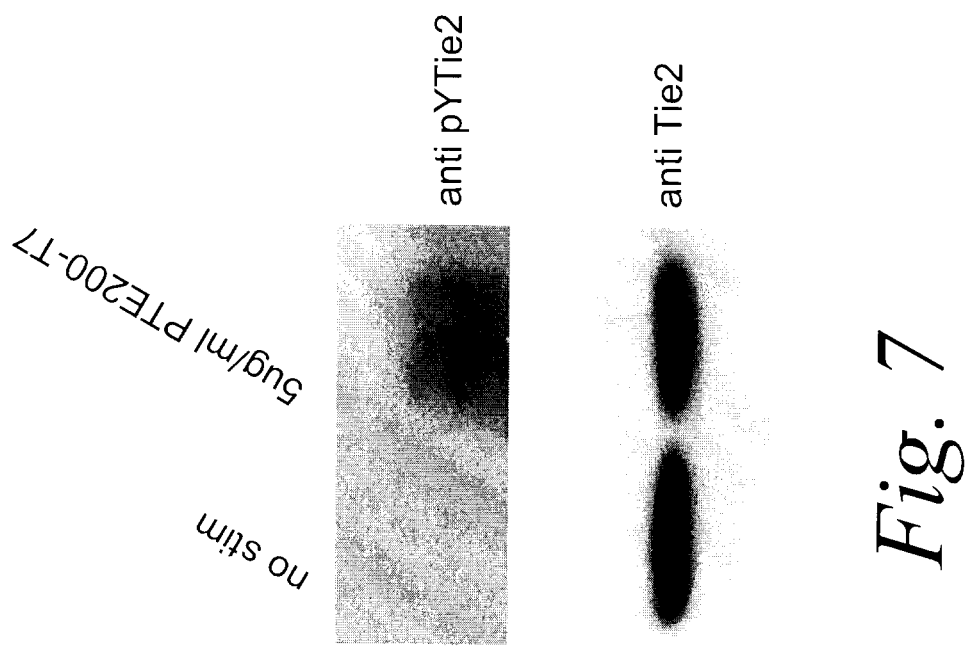
FIG. 7 is an immunoblot analysis of lysates from bovine vascular endothelial cells (bVECs) stimulated with PTE200-T7 (tetrameric PEG-linked T7, 20,000 Da MW) at 5 µg/ml, showing that treatment with PTE200-T7 results in activation of Tie 2.
Figure 8:
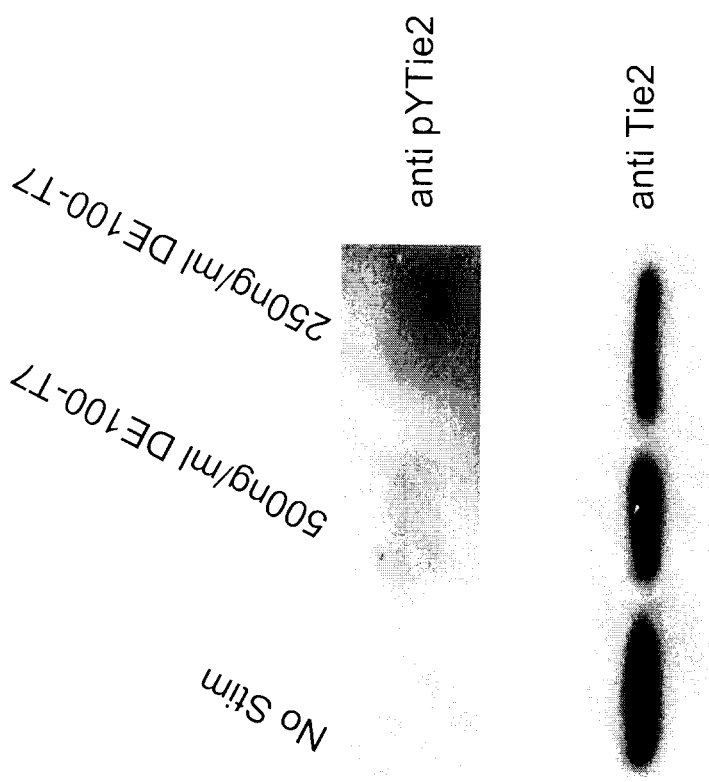
FIG. 8 is an immunoblot analysis of lysates from bovine vascular endothelial cells (bVECs) stimulated with DE100-T7 (dimeric PEG-linked T7, 10,000 Da MW) at 250 ng/ml or 500 ng/ml, showing that treatment with DE100-T7 results in activation of Tie 2.

The results for stimulation with 5 μg/ml of PTE200-T7 are shown in FIG. 7 and the results for stimulation with either 250 ng/ml or 500 ng/ml DE100-T7 are shown in FIG. 8. The results show that increased levels of Tie2 activation, as detected by phosphorylation at Y992, occurred in the samples treated with PTE200-T7 or DE100-T7 but not in the samples treated with PBS, demonstrating the both PEG-T7 Vasculotide compounds are capable of activating the Tie 2 receptor in vitro.

Example 11

In Vivo Tie 2 Activation by PEG-Vasculotide

In this example, the ability of the PEG-T7 Vasculotide compounds, prepared as described in Example 9, to activate the Tie 2 receptor in vivo was examined by administering the compounds to mice, followed by examination of lung cell tissue for activation of Tie 2 and downstream pathways, since lung tissue contains a very high vascular density and thus serves as an ideal organ to examine activation of Tie 2.

Twelve week old wild type CD1 mice were injected intravenously in the tail vein with PTE200-T7 Vaculotide (5 μg or 75 μg), DE200-T7 Vasculotide (10 μg or 50 μg) or DE100-T7 Vasculotide (5 μg or 100 μg) suspended in sterile PBS or PBS alone. After 20 minutes the mice were sacrificed by way of cervical dislocation and the lungs were removed and frozen at −80° C. for analysis. Defrosted lung tissue was lysed in RIPA lysis buffer (described further in Example 10). Protein concentrations were determined for each sample and equal quantities of protein were immunoprecipitated for Tie 2 (Pharminogen, anti-Tie 2 clone 33.1 and protein G sepharose, Amersham). Immunoprecipitates were electrophoretically resolved and transferred to PVDF membrane for immunoblot analysis. Total phosphorylation of Tie 2 was determined using an anti pY antibody (Upstate Biotechnology, clone 4G10). Additionally equal quantities of whole cell lysate were separated electrophoretically and transferred to PVDF membrane for immunoblot analysis with anti pan Mapk, anti phospho Mapk, anti pan Akt, anti pS473 Akt, as described previously in Example 3.

Figure 9:
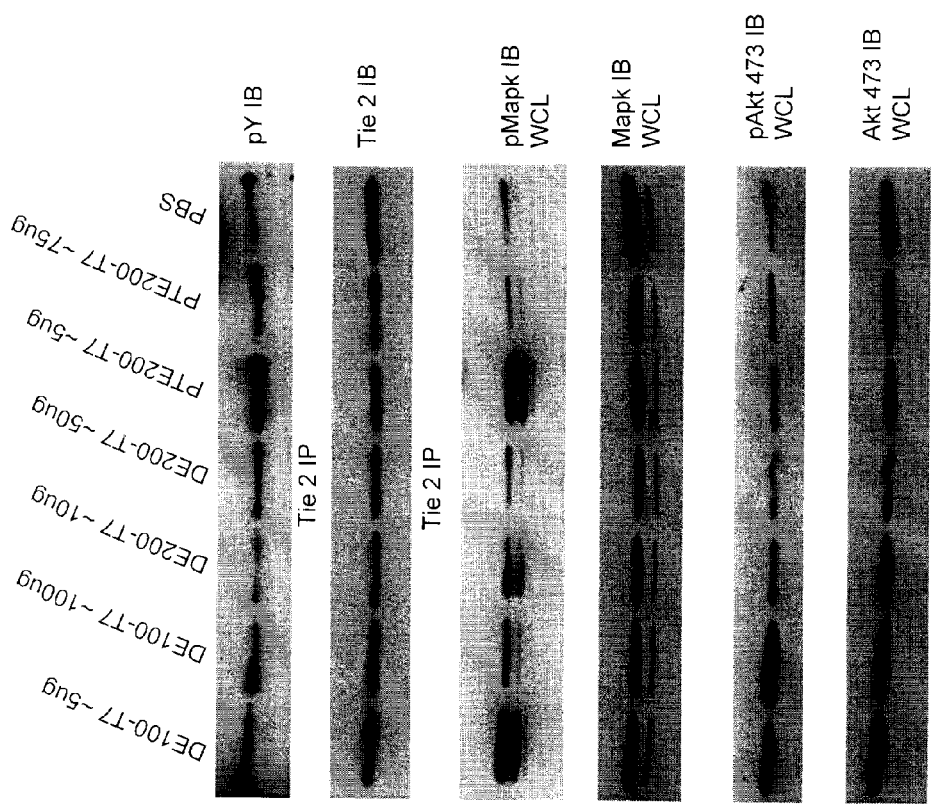
FIG. 9 is an immunoprecipitation/immunoblot analysis of lung tissue lysates from CD1 mice stimulated in vivo with DE100-T7 (dimeric PEG-linked T7, 10,000 Da MW) at 5 µg or 100 µg, DE200-T7 (dimeric PEG-linked T7, 20,000 Da MW) at 10 µg or 50 µg), PTE200-T7 (tetrameric PEG-linked T7) at 5 µg or 75 µg, or PBS, examining phosphorylation of Tie 2 and of downstream pathway markers MAPK and AKT.

The results are shown in FIG. 9. Increases in total Tie 2 activation were noted in mice that received dimeric PEG-T7, MW 10,000 Da (DE100-T7) and tetrameric PEG-T7, MW 20,000 Da (PTE200-T7). As well, pathways downstream of Tie 2 including Mapk and Akt were activated upon treatment with dimeric PEG-T7, MW 10,000 Da and tetrameric PEG-T7, MW 20,000 Da, but not dimeric PEG-T7, MW 20,000 (DE200-T7), suggesting that appropriate T7 peptide spacing is critical for optimal Tie 2/Mapk/Akt activation (see pMapk and pS473Akt compared to PBS control). Furthermore, consistent with data generated using the avidin-biotin tetrameric Vasculotide, it was observed that lower doses of PEG-T7 Vasculotide promoted a more roboust activation of Tie 2 and downstream signaling events.

Example 12

Preparation and Characterization of Monoclonal Antibodies Specific for the T7 Peptide In this example, monoclonal antibodies specific for the T7 peptide were prepared and characterized. T7 peptide was covalently conjugated to BSA or KLH using Pierce Chemical Company's "Imject Maleimide Activated Immunogen Conjugation Kit with mcKLH and BSA" according to kit instructions. Injection of the immunogen into 4 week old female BALB/C mice, collection of serum, preparation of hybridomas and screening of antibodies were all performed according to kit instructions and under the animal care guidelines of Sunnybrook Research Institute (Toronto, Ontario, Canada).

Hybridoma supernatants initially were screened by standard ELISA using T7-BSA as the antigen, the results of which are shown below in Table 1:

TABLE 1

ELISA Screening Results for Hybridoma Supernatants

| Hybridoma for T7 | Single Cell Clone | ELISA result | Background |
|---|---|---|---|
| F11.4F2 |  | 0.258 | 0.037 |
| F11.4H6 | yes | 0.641 | 0.039 |
| F11.2C11 | yes | 0.307 | 0.043 |
| F11.9G8 |  | 0.379 | 0.033 |
| F11.15F3 |  | 0.374 | 0.033 |
| F11.3E4 | yes | 0.249 | 0.047 |
| F11.7G4 |  | 0.182 | 0.4 |
| F11.7E7 |  | 0.339 | 0.035 |
| F11.7B12 |  | 0.186 | 0.035 |
| F11.7D6 |  | 0.168 | 0.036 |
| F11.13G12 |  | 0.117 | 0.034 |
| F11.12B7 |  | 0.278 | 0.037 |
| F11.13D4 | yes | 0.955 | 0.04 |
| F11.14A4 |  | 195 | 0.036 |
| F11.9B11 |  | 0.105 | 0.034 |
| F11.2G6 |  | 0.208 | 0.051 |

All clones that tested positive during initial screening are presented in Table 1. All single cell clones were further tested to assess specificity.

Figure 10:
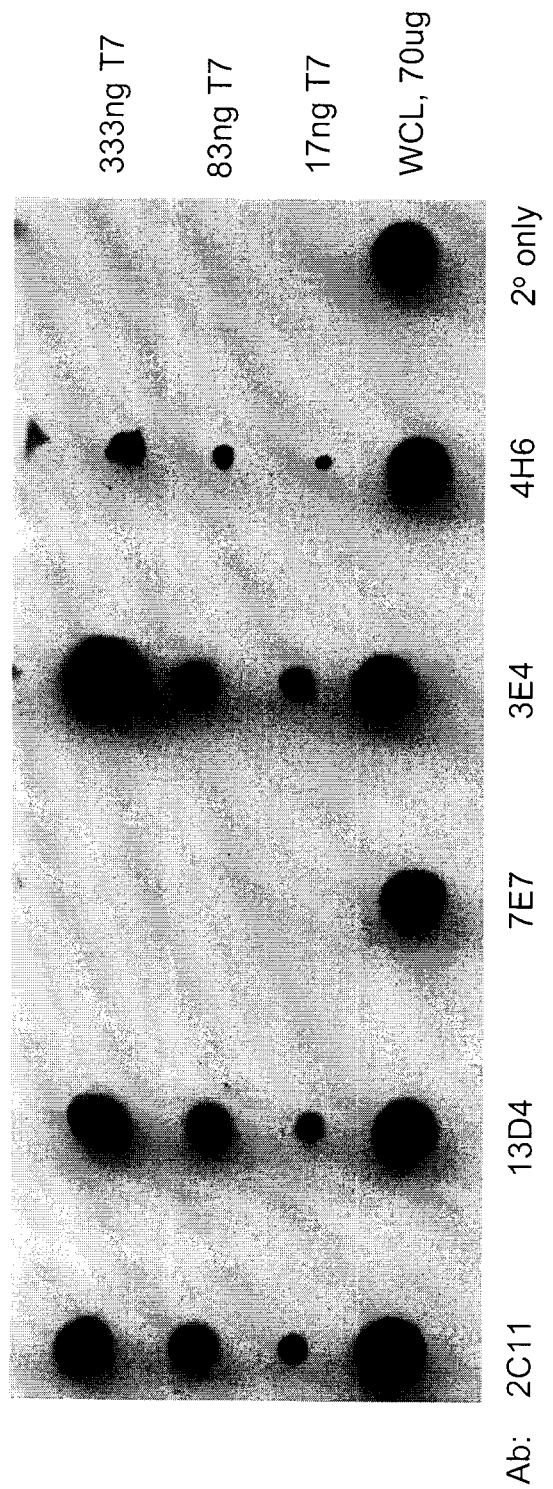
FIG. 10 is a dot blot analysis to assess the specificity of mouse monoclonal antibodies engineered to detect T7 peptide using PTE200-T7 as the antigen.

Dot blot analysis was performed to assess the specificity of mouse monoclonal hybridomas engineered to detect the T7 peptide. Tetrameric PEG-T7 (PTE200-T7) was spotted onto a PVDF membrane at 17 ng, 83 ng and 333 ng (these quantities represent the overall T7 content applied to the membrane and do not account for the weight of the PEG). The membrane was allowed to dry at which point it was block in 5% non-fat skim milk and probed with the 2C11, 13D4, 7E7, 3E4 and 4H6 hybridoma supernatants at 1:500 dilution. Detection was performed according to standard practices using a goatn anti-mouse horse radish peroxidase secondary antibody at 1:10,000 dilution. The results are shown in FIG. 10. All clones except for 7E7 were capable of detecting tetrameric PEG-T7 at the tested concentrations. Tissue whole cell lysate (WCL, 70 µg) was included as a specificity control and the results indicate that the secondary antibody used in the detection non-specifically interacts with some component of the whole cell lysate.

Figure 11:
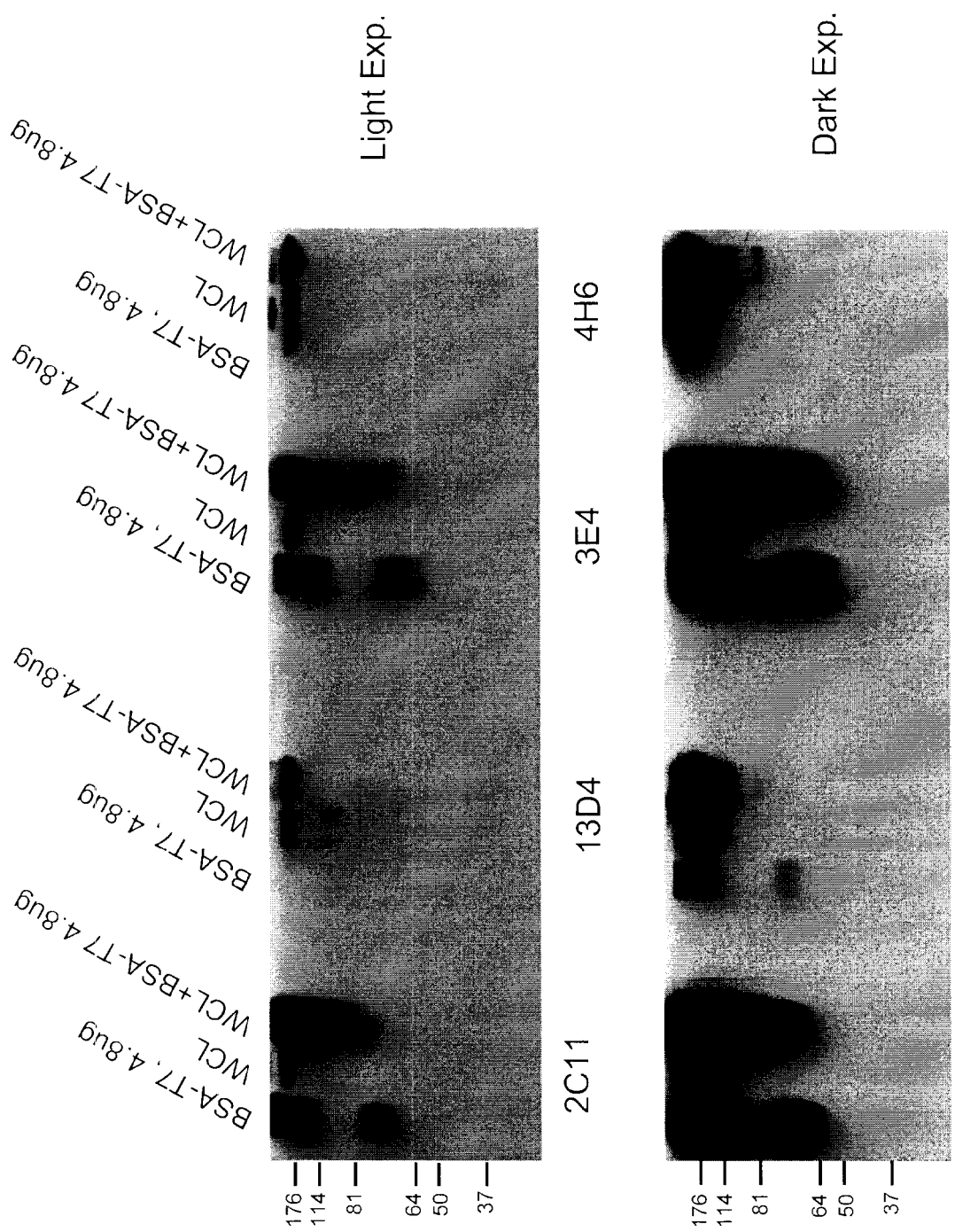
FIG. 11 is an immunoblot analysis to assess the specificity of mouse monoclonal antibodies engineered to detect T7 peptide using T7-BSA as the antigen.

To further assess the binding of the 2C11, 13D4, 3E4 and 4H6 anti-T7 mouse monoclonal antibodies, an immunoblot analysis was performed with T7-BSA as the antigen. To prepare T7-BSA antigen, T7 peptide was covalently conjugated to bovine serum albumin using the "Imject Maleimide Activated Immunogen Conjugation Kit with mcKLH and BSA" supplied by Pierce according to manufacturers instructions. The resultant T7-BSA, alone or spiked with 100 µg of mouse lung whole cell lysate, was electrophoretically resolved (in non-reducing conditions) and transferred to PVDF membrane for immunoblot analysis. The PVDF membranes were probed with the 2C11, 13D4, 3E4 and 4H6 hybridoma supernatant according to standard immunoblot practice. The results are shown in FIG. 11. All clones tested were capable of detecting T7-BSA (total amount of T7 was equal to 75 ng) to varying degrees. The immunoblots showed distinct bands at approximately 70 kDa, 140 kDa, and 210 kDa which are thought to represent non-reduced aggregates of BSA-T7. Tested clones also detected a single protein in the lung whole cell lysate of approximately 200 kDa.

What is claimed is:

1. A composition comprising a multimeric form of Tie 2 binding peptide monomers, wherein the multimeric form has Tie 2 agonist activity, wherein each peptide monomer comprises:
   (i) a T7 peptide (SEQ ID NO:1) or a T7 modified peptide (SEQ ID NO:2);
   (ii) a GA3 peptide (SEQ ID NO:3) or a GA3 modified peptide (SEQ ID NO:4);
   (iii) a T4 peptide (SEQ ID NO:9) or a T4 modified peptide (SEQ ID NO:10);
   (iv) a T6 peptide (SEQ ID NO:7) or a T6 modified peptide (SEQ ID NO:8); or
   (v) a T8 peptide (SEQ ID NO:5) or a T8 modified peptide (SEQ ID NO:6);
   and wherein the Tie 2 binding peptide monomers are multimerized via a linking moiety, spacer and/or multimerizing agent.

2. The composition of claim 1, wherein the multimeric form is a tetramer.

3. The composition of claim 1, wherein the multimeric form is a dimer.

4. The composition of claim 1, wherein the multimeric form comprises six, eight, ten or twelve units of the Tie 2 binding peptide monomer.

5. The composition of claim 1, wherein the multiple Tie 2 binding peptide monomers are covalently linked to the spacer.

6. The composition of claim 1, which comprises a tetramer form of Tie 2 binding peptide monomers, wherein each Tie 2 binding peptide monomer comprises a structure: A-B-C, wherein:
   A comprises the Tie 2 binding peptide selected from a T7 peptide (SEQ ID NO: 1), a T7 modified peptide (SEQ ID NO:2), a GA3 peptide (SEQ ID NO: 3) and a modified GA3 peptide (SEQ ID NO:4);
   B comprises a polyethylene glycol (PEG) spacer; wherein the spacer contains 2-12 PEG units; and
   C comprises a biotin group,
   wherein the four A-B-C structures are associated with a tetramer agent, D, to create the tetramer form, the tetramer agent, D, being selected from the group consisting of avidin, streptavidin and neutravidin.

7. The composition of claim 1, which comprises a peptide dimer, comprising: (a) a first Tie 2 binding peptide monomer; (b) a second Tie 2 binding peptide monomer; and (c) a linking moiety connecting said first and second Tie 2 binding peptide monomers, wherein said peptide dimer binds to and activates the Tie 2 receptor and wherein the linking moiety comprises a polyethylene glycol (PEG) of 3,000 Daltons to 10,000 Daltons.

8. The composition of claim 7, wherein the first Tie 2 binding peptide monomer and the second Tie 2 binding peptide monomer are T7 peptides (SEQ ID NO:1), modified T7 peptides (SEQ ID NO:2) or a combination thereof.

9. The composition of claim 1, which comprises a peptide tetramer, comprising: (a) a first Tie 2 binding peptide monomer; (b) a second Tie 2 binding peptide monomer; (c) a third Tie 2 binding peptide monomer; (d) a fourth Tie 2 binding peptide monomer; and (e) a linking moiety connecting said first, second, third and fourth Tie 2 binding peptide monomers, wherein said peptide tetramer binds to and activates the Tie 2 receptor; wherein the linking moiety comprises one or more water soluble polymers covalently bound to the first, second, third and fourth Tie 2 binding peptide monomers.

10. The composition of claim 9, wherein the first, second, third and fourth Tie 2 binding peptide monomers are T7 peptides (SEQ ID NO: 1), modified T7 peptides (SEQ ID NO: 2), or a combination thereof.

11. The composition of claim 9, wherein the water soluble polymer is a branched chain polyethylene glycol (PEG).

12. A composition comprising a tetrameric form of a Tie 2 binding peptide monomer, wherein the tetrameric form has Tie 2 agonist activity, and comprises: (a) a first Tie 2 binding peptide monomer; (b) a second Tie 2 binding peptide monomer; (c) a third Tie 2 binding peptide monomer; (d) a fourth Tie 2 binding peptide monomer; and (e) a linking moiety connecting said first, second, third and fourth Tie 2 binding peptide monomers, wherein said peptide tetramer binds to and activates the Tie 2 receptor; wherein the first, second, third and fourth Tie 2 binding peptide monomers are T7 peptides (SEQ ID NO: 1), T7 modified peptides (SEQ ID NO:2), GA3 peptides (SEQ ID NO:3) or GA3 modified peptides (SEQ ID NO:4), or a combination thereof; and wherein the linking moiety comprises a branched polyethylene glycol (PEG) of 3,000 Daltons to 20,000 Daltons.

13. The composition of claim 12, wherein the first, second, third and fourth peptides are T7 peptides (SEQ ID NO: 1), T7 modified peptides (SEQ ID NO:2), or a combination thereof.

\* \* \* \* \*